United States Patent
Ronan et al.

(10) Patent No.: US 7,592,365 B2
(45) Date of Patent: Sep. 22, 2009

(54) SUBSTITUTED PYRROLES, COMPOSITIONS CONTAINING SAME, METHOD FOR MAKING SAME AND USE THEREOF

(75) Inventors: Baptiste Ronan, Clamart (FR); Michel Tabart, La Norville (FR); Catherine Souaille, Choisy le Roi (FR); Fabrice Viviani, Louvres (FR); Eric Bacque, Gif sur Yvette (FR); Jean-Philippe Letallec, Paris (FR); Pascal Desmazeau, Tigery (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/832,208

(22) Filed: Aug. 1, 2007

(65) Prior Publication Data

US 2008/0167368 A1 Jul. 10, 2008

Related U.S. Application Data

(63) Continuation of application No. PCT/FR2006/000286, filed on Feb. 8, 2006.

(30) Foreign Application Priority Data

Feb. 10, 2005 (FR) .................... 05 01354

(51) Int. Cl.
A61K 31/4025 (2006.01)
A61K 31/166 (2006.01)
C12N 9/99 (2006.01)
C07C 233/57 (2006.01)
C07D 207/34 (2006.01)

(52) U.S. Cl. ........................ 514/423; 514/613; 435/184; 548/537; 564/189

(58) Field of Classification Search ................ 514/423, 514/613; 548/537; 435/184; 564/189
See application file for complete search history.

(56) References Cited

U.S. PATENT DOCUMENTS

| 7,183,285 | B2 * | 2/2007 | Griffin et al. ............... 514/256 |
| 2004/0138269 | A1 | 7/2004 | Sun et al. |
| 2005/0261354 | A1 | 11/2005 | Griffin et al. |

FOREIGN PATENT DOCUMENTS

| CA | 2 546 334 | 6/2005 |
| WO | WO 02/079193 A1 | 10/2002 |
| WO | WO 03/072541 A2 | 9/2003 |
| WO | WO 2005/049603 A1 | 6/2005 |
| WO | WO 2006/082309 A1 | 8/2006 |

OTHER PUBLICATIONS

Kinase, Wikipedia.*
FAK, Wikipedia.*
KDR, Wikipedia.*
Tie2, Wikipedia.*
U.S. Appl. No. 11/832,206, filed Aug. 1, 2007, Ronan et al.

* cited by examiner

*Primary Examiner*—Yong Chu
(74) *Attorney, Agent, or Firm*—Kelly L. Bender

(57) ABSTRACT

The disclosure concerns substituted pyrroles of formula (I):

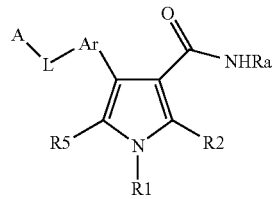

wherein A, L, Ar, R1, R2, R5, and Ra are as defined in the disclosure, compositions containing the same, methods for making the same and uses thereof, in particular as anti-cancer agents.

20 Claims, No Drawings

SUBSTITUTED PYRROLES, COMPOSITIONS CONTAINING SAME, METHOD FOR MAKING SAME AND USE THEREOF

The present invention relates in particular to novel chemical compounds, particularly novel substituted pyrroles, compositions containing them, and their use as medicaments.

More particularly, the invention relates to novel specific pyrroles having anticancer activity via the modulation of the activity of proteins, in particular kinases.

To date, most of the commercial compounds used in chemotherapy have major problems of side effects and of tolerance by the patients. These effects could be limited in so far as the medicaments used act selectively on cancer cells, excluding healthy cells. One of the solutions for limiting the undesirable effects of chemotherapy may therefore consist in the use of medicaments acting on metabolic pathways or constituent components of these pathways, predominantly expressed in cancer cells, and which might not or might only rarely be expressed in healthy cells.

Protein kinases are a family of enzymes which catalyse the phosphorylation of hydroxyl groups of specific residues of proteins such as tyrosine, serine or threonine residues. Such phosphorylations can greatly modify the function of the proteins; thus, protein kinases play a major role in the regulation of a large variety of cellular processes, including in particular metabolism, cell proliferation, cell differentiation, cell migration or cell survival. Among the various cellular functions in which the activity of a protein kinase is involved, some processes represent attractive targets for treating cancer diseases and other diseases.

Thus, one of the objects of the present invention is to provide compositions having anticancer activity, which act in particular on kinases. Among the kinases for which activity modulation is sought, FAK, KDR and Tie2 are preferred.

These products have the following formula (I):

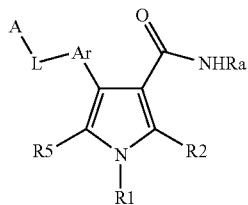

Formula (I)

in which:
1) A and Ar are independently selected from the group consisting of: aryl, heteroaryl, heterocyclyl, substituted aryl, substituted heteroaryl, substituted heterocyclyl, cycloalkyl, substituted cycloalkyl;
2) L is selected from the group consisting of: NH, CO—NH, NH—CO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$, NH—CO—CH$_2$—CO—NH;
3) Ra is selected from the group consisting of H, alkyl and cycloalkyl;
4) R1 is selected from the group consisting of: H, R, COR, SO$_2$R, in which R is chosen from H, OR"$_4$, NR"$_5$R"$_6$, (C1-C6)alkyl, cycloalkyl, heterocyclyl, substituted heterocyclyl, aryl, substituted aryl, heteroaryl, substituted heteroaryl, in which R"4 is chosen from H, phenyl, alkyl, and in which R"5 and R"6 are independently selected from the group consisting of H, R OR"$_4$, (C1-C6)alkyl, cycloalkyl, heterocyclyl, substituted heterocyclyl, aryl, substituted aryl, heteroaryl, substituted heteroaryl or alternatively R"5 and R"6 are linked to each other to form a 5- to 8-membered saturated ring containing from 0 to 3 heteroatoms chosen from O, S and N;
5) R2 and R5 are independently selected from the group consisting of: H, halogen, R'2, CN, O(R'2), OC(O)(R'2), OC(O)N(R'2)(R'3), OS(O$_2$)(R'2), N(R'2)(R'3), N═C(R'2)(R'3), N(R'2)C(O)(R'3), N(R'2)C(O)O(R'3), N(R'4)C(O)N(R'2)(R'3), N(R'4)C(S)N(R'2)(R'3), N(R'2)S(O$_2$)(R'3), C(O)(R'2), C(O)O(R'2), C(O)N(R'2)(R'3), C(═N(R'3))(R'2), C(═N(OR'3))(R'2), S(R'2), S(O)(R'2), S(O$_2$)(R'2), S(O$_2$)O(R'2), S(O$_2$)N(R'2)(R'3); in which each R'2, R'3, R'4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl; in which, when R'2 and R'3 are each different from H and simultaneously present on R2 or on R3, they may be linked to each other to form a ring containing from 0 to 3 heteroatoms chosen from O, S and N.

Preferred products of formula (I) correspond to the following definition:

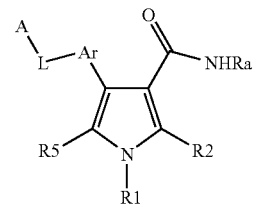

Formula (I)

in which:
1) A and Ar are as defined above;
2) R1 is H;
3) L is selected from the group consisting of: NHCO, NH—CO—NH, NH, NHSO$_2$, NHCO—CH$_2$—CONH;
4) Ra is selected from H and methyl;
5) R2 and R5 are as defined above.

In the products of formula (I), Ar-L-A is advantageously:

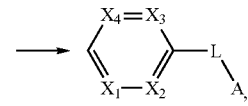

in which each X1, X2, X3 and X4 is independently chosen from N and C—R'5, in which R'5 has the same definition as R2.

Substituents R'5 selected from the group consisting of H, F, Cl, methyl, NH$_2$, OMe, OCF$_3$, and CONH$_2$ are preferred.

Preferred substituents R2 and R5 are independently selected from the group consisting of: H, halogen, R'2, OR'2, NHR'2, NHCOR'2, NHCONHR'2, NHSO$_2$R'2. R2 and R5 are preferably H.

A preferred substituent Ra is H.

Preferred substituents L-A are advantageously chosen from NH—CO—NH-A and NH—SO$_2$-A.

A particularly effective combination L-A is obtained when L-A is NHCONH-A.

Products in accordance with the invention preferably have a substituent A which is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl, and benzothiazolyl; optionally substituted.

More preferably, A is chosen from phenyl, pyrazolyl and isoxazolyl; optionally substituted.

The substituent A is very advantageously substituted with a first substituent selected from the group consisting of alkyl, alkylene, alkynyl, aryl, heteroaryl, O-alkyl, O-aryl, O-heteroaryl, S-alkyl, S-aryl, S-heteroaryl, each being optionally substituted with a substituent chosen from (C1-C3)alkyl, halogen, O—(C1-C3)alkyl.

The substituent A is preferably substituted with a second substituent chosen from the group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9); in which R8 and R9 are independently chosen from H, (C1-C3)alkyl, halogenated (C1-C3)alkyl, (C1-C3)alkylOH, (C1-C3)alkylNH$_2$, (C1-C3)alkylCOOM, (C1-C3)alkylSO$_3$M; in which, when R8 and R9 are simultaneously different from H, they may be linked to form a 5- to 7-membered ring containing from 0 to 3 heteroatoms; in which M is H or an alkali metal cation chosen from Li, Na and K; and in which R10 is H or an optionally substituted nonaromatic heterocycle comprising 2 to 7 carbon atoms, and 1 to 3 heteroatoms chosen from N, O and S.

Particularly preferred substituents A are chosen from phenyl, pyrazolyl and isoxazolyl; it being possible for the said substituents A to be substituted with halogen, (C1-C4)alkyl, halogenated (C1-C3)alkyl, O—(C1-C4)alkyl, S—(C1-C4)alkyl, halogenated O—(C1-C4)alkyl and halogenated S—(C1-C4)alkyl. When A is disubstituted, the two substituents of A may form a 5- to 7-membered ring containing from 0 to 3 heteroatoms.

The products of Examples 1 to 41 are the subject of the present invention.

A product in accordance with the invention may be provided in a form which is:
1) non-chiral, or
2) racemic, or
3) enriched with one stereoisomer, or
4) enriched with one enantiomer;

and may be optionally salified.

A product in accordance with the invention may be used for the manufacture of a medicament useful for treating a pathological state, in particular a cancer.

The present invention also relates to the therapeutic compositions comprising a product according to the invention, in combination with a pharmaceutically acceptable excipient according to the mode of administration chosen. The pharmaceutical composition may be provided in solid, liquid or liposome form.

Powders, gelatin capsules and tablets may be mentioned among the solid compositions. The solid forms protected against the acidic medium of the stomach may also be included among the oral forms. The carriers used for the solid forms consist in particular of inorganic carriers such as phosphates and carbonates, or of organic carriers such as lactose, celluloses, starch or polymers. The liquid forms consist of solutions, suspensions or dispersions. They contain, as dispersive carrier, either water, an organic solvent (ethanol, NMP and the like) or mixtures of surfactants and solvents or of complexing agents and solvents.

The liquid forms will be preferably injectable and, as such, will have a formulation acceptable for such a use.

Acceptable routes of administration by injection include the intravenous, intraperitoneal, intramuscular, and subcutaneous routes, the intravenous route being usually preferred.

The administered dose of the compounds of the invention will be adjusted by the practitioner according to the route of administration to the patient and the condition of the latter.

The compounds of the present invention may be administered alone or as a mixture with other anticancer agents. Among the possible combinations, there may be mentioned:

alkylating agents and in particular cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine platinum derivatives such as in particular cisplatin, carboplatin or oxaliplatin antibiotic agents such as in particular bleomycin, mitomycin, dactinomycine antimicrotubule agents such as in particular vinblastine, vincristine, vindesine, vinorelbine, taxoids (paclitaxel and docetaxel)

anthracyclines such as in particular doxorubicin, daunorubicin, idarjbicin, epirjbicin, mitoxantrone, iosoxantrone inhibitors of groups I and II topoisomerases such as etoposide, teniposide, amsacrine, irinotecan, topotecan and tomudex fluoropyrimidines such as 5-fluorouracil, UFT, floxuridine cytidine analogues such as 5-azacytidine, cytarabine, gemcitabine, 6-mercaptomurine, 6-thioguanine adenosine analogues such as pentostatin, cytarabine or fludarabine phosphate methotrexate and folinic acid enzymes and various compounds such as L-asparaginase, hydroxyurea, trans-retinoic acid, suramine, dexrazoxane, amifostine, herceptine and oestrogenic or androgenic hormones antivascular agents such as combretastatin derivatives, for example CA4P, charlcones or colchicine, for example ZD6126, and their prodrugs.

It is also possible to combine a radiation treatment with the compounds of the present invention. These treatments may be administered simultaneously, separately or sequentially. The treatment will be adapted by the practitioner according to the patient to be treated.

The products of the invention are useful as agents inhibiting a reaction catalysed by a kinase. FAK, KDR and Tie2 are kinases for which the products of the invention will be particularly useful as inhibitors.

The reasons for which these kinases are chosen are given below:

FAK

FAK is a cytoplasmic tyrosine kinase which plays a major role in the transduction of the signal transmitted by integrines, a family of heterodimeric receptors for cell adhesion. FAK and integrines are colocalized in perimembrane structures called adhesion plaques. It has been shown, in numerous cell types, that the activation of FAK and its phosphorylation on tyrosine residues, and in particular its autophosphorylation on tyrosine 397, were dependent on the binding of integrines to their extracellular ligands and therefore induced during cell adhesion [Kornberg L, et al. J. Biol. Chem. 267(33): 23439-442. (1992)]. Autophosphorylation on tyrosine 397 of FAK represents a binding site for another tyrosine kinase, Src, via its SH2 domain [Schaller et al. Mol. Cell. Biol. 14; 1680-1688. 1994; Xing et al. Mol. Cell. Biol. 5; 413-421. 1994]. Src can then phosphorylate FAK on tyrosine 925, thus recruiting the adaptor protein Grb2 and inducing in some cells the activation of the ras and MAP kinase route involved in the control of cell proliferation [Schlaepfer et al. Nature; 372: 786-791. 1994; Schlaepfer et al. Prog. Biophy. Mol. Biol. 71:435-478. 1999; Schlaepfer and Hunter, J. Biol. Chem. 272:13189-13195. 1997]. The activation of FAK can also induce the jun NH2-terminal kinase (JNK) signalling pathway and result in the progression of cells to the G1 phase of the cell cycle [Oktay et al., J. Cell. Biol. 145; 1461-1469. 1999]. Phosphatidylinositol-3-OH kinase (PI3-kinase) also binds to FAK on tyrosine 397 and this interaction could be necessary for the activation of PI3-kinase [Chen and Guan, Proc. Nat. Acad. Sci. USA. 91: 10148-10152. 1994; Ling et al. J. Cell. Biochem. 73; 533-544. 1999]. The FAK/Src complex phosphorylates various substrates such as paxillin and p130CAS in the fibroblasts [Vuori et al. Mol. Cell. Biol. 16: 2606-2613. 1996].

The results of numerous studies support the hypothesis that inhibitors of FAK could be useful in the treatment of cancer. Studies have suggested that FAK could play a major role in cell proliferation and/or survival in vitro. For example, in CHO cells, some authors have demonstrated that the overexpression of p125FAK leads to an acceleration of the G1 to S transition, suggesting that p125FAK promotes cell proliferation [Zhao J.-H et al. *J. Cell Biol.* 143:1997-2008. 1998]. Other authors have shown that tumour cells treated with antisense oligonucleotides of FAK lose their adhesion and enter into apoptosis (Xu et al, Cell Growth Differ. 4:413-418. 1996). It has also been demonstrated that FAK promotes the migration of cells in vitro. Thus, fibroblasts deficient for the expression of FAK (knockout mice for FAK) exhibit a round morphology, cell migration deficiencies in response to chemotactic signals and these defects are suppressed by a re-expression of FAK [D J. Sieg et al., J. Cell Science. 112: 2677-91. 1999]. The overexpression of the C-terminal domain of FAK (FRNK) blocks the stretching of adherent cells and reduces cell migration in vitro [Richardson A. and Parsons J. T. Nature. 380:538-540. 1996]. The overexpression of FAK in CHO or COS cells, or in human astrocytoma cells promotes migration of the cells. The involvement of FAK in promoting the proliferation and migration of cells in numerous cell types in vitro suggests the potential role of FAK in neoplasic processes. A recent study has indeed demonstrated the increase in the proliferation of tumour cells in vivo after induction of the expression of FAK in human astrocytoma cells [Cary L. A. et al. J. Cell Sci. 109:1787-94. 1996; Wang D et al. J. Cell Sci. 113:4221-4230. 2000]. Furthermore, immunohistochemical studies of human biopsies have demonstrated that FAK was overexpressed in prostate, breast, thyroid, colon, melanoma, brain and lung cancers, the level of FAK expression being directly correlated with tumours exhibiting the most aggressive phenotype [Weiner T M, et al. Lancet. 342(8878):1024-1025. 1993; Owens et al. Cancer Research. 55:2752-2755. 1995; Maung K. et al. Oncogene. 18:6824-6828.1999; Wang D et al. J. Cell Sci. 113:4221-4230. 2000].

KDR

KDR (Kinase insert Domain Receptor) also called VEGF-R2 (Vascular Endothelial Growth Factor Receptor 2), is expressed solely in endothelial cells. This receptor binds to the angiogenic growth factor VEGF and thus serves as mediator for a transduction signal via the activation of its intracellular kinase domain. The direct inhibition of VEGF-R2 kinase activity makes it possible to reduce the phenomenon of angiogenesis in the presence of exogenous VEGF (Vascular Endothelial Growth Factor) (Strawn et al., *Cancer Research,* 1996, vol. 56, p. 3540-3545). This process was demonstrated in particular with the aid of VEGF-R2 mutants (Millauer et al., *Cancer Research,* 1996, vol. 56, p. 1615-1620). The VEGF-R2 receptor appears to have no other function in adults than that linked to the angiogenic activity of VEGF. Consequently, a selective inhibitor of the kinase activity of VEGF-R2 should demonstrate only very little toxicity.

In addition to this central role in the dynamic angiogenic process, recent results suggest that the expression of VEGF contributes to the survival of tumour cells after chemo- and radiotherapies, underlying the potential synergy of inhibitors of KDR with other agents (Lee et al. *Cancer Research,* 2000, vol. 60, p. 5565-5570).

Tie2

Tie-2 (TEK) is a member of a tyrosine kinase receptor family specific for endothelial cells. Tie2 is the first receptor with tyrosine kinase activity for which both the agonist (angiopoietin 1 or Ang1), which stimulates auto-phosphorylation of the receptor and cell signalling [S. Davis et al (1996) *Cell* 87, 1161-1169], and the antagonist (angiopoietin 2 or Ang2) [P. C. Maisonpierre et al. (1997) *Science* 277, 55-60] are known. Angiopoietin 1 can synergize with VEGF in the final stages of neoangiogenesis [*Asahara T. Circ. Res.* (1998) 233-240]. Knockout experiments and transgenic manipulations of the expression of Tie2 or of Ang1 lead to animals which have vascularization defects [D. J. Dumont et al (1994) *Genes Dev.* 8, 1897-1909 and C. Suri (1996) *Cell* 87, 1171-1180]. The binding of Ang1 to its receptor leads to autophosphorylation of the kinase domain of Tie2 which is essential for neovascularization and for the recruitment and interaction of vessels with the pericytes and the smooth muscle cells; these phenomena contribute to the maturation and the stability of the newly formed vessels [P. C. Maisonpierre et al (1997) *Science* 277, 55-60]. Lin et al (1997) *J. Clin. Invest.* 100, 8: 2072-2078 and Lin P. (1998) *PNAS* 95, 8829-8834, have shown inhibition of tumour growth and vascularization, and a decrease in lung metastases, during adenoviral infections or injections of the extracellular domain of Tie-2 (Tek) in models of breast tumour xenographs and of melanoma.

Inhibitors of Tie2 can be used in situations where neovascularization occurs inappropriately (that is to say in diabetic retinopathy, chronic inflammation, psoriasis, Kaposi's sarcoma, chronic neovascularization due to macular degeneration, rheumatoid arthritis, infantile haemangioma and cancers).

DEFINITIONS

The term "halogen" refers to an element chosen from F, Cl, Br, and I.

The term "alkyl" refers to a linear or branched, saturated hydrocarbon substituent having from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl, and dodecyl are examples of an alkyl substituent.

The term "alkylene" refers to a linear or branched hydrocarbon substituent having one or more unsaturations, having from 2 to 12 carbon atoms. The substituents ethylenyl, 1-methylethylenyl, prop-1-enyl, prop-2-enyl, Z-1-methylprop-1-enyl, E-1-methylprop-1-enyl, Z-1,2-dimethyl-prop-1-enyl, E-1,2-dimethylprop-1-enyl, but-1,3-dienyl, 1-methylidenyl-prop-2-enyl, Z-2-methylbut-1,3-dienyl, E-2-methylbut-1,3-dienyl, 2-methyl-1-methylidenyl-prop-2-enyl, undec-1-enyl and undec-10-enyl are examples of an alkylene substituent.

The term "alkynyl" refers to a linear or branched hydrocarbon substituent having at least two unsaturations carried by a pair of vicinal carbon atoms, having from 2 to 12 carbon atoms. The substituents ethynyl; prop-1-ynyl; prop-2-ynyl; and but-1-ynyl are examples of an alkynyl substituent.

The term "aryl" refers to a mono- or polycyclic aromatic substituent having from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of an aryl substituent.

The term "heteroaryl" refers to a mono- or polycyclic heteroaromatic substituent having from 1 to 13 carbon atoms and from 1 to 4 heteroatoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinoleyl; isoquinoleyl; carbazolyl; and acridyl are examples of a heteroaryl substituent.

The term "heteroatom" refers here to an at least divalent atom, different from carbon. N; O; S; and Se are examples of heteroatoms.

The term "cycloalkyl" refers to a saturated or partially unsaturated cyclic hydrocarbon substituent having from 3 to 12 carbon atoms. The substituents cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronaphthyl are examples of a cycloalkyl substituent.

The term "heterocyclyl" refers to a saturated or partially unsaturated cyclic hydrocarbon substituent having from 1 to 13 carbon atoms and from 1 to 4 heteroatoms. Preferably, the saturated or partially unsaturated cyclic hydrocarbon substituent will be monocyclic and will contain 4 or 5 carbon atoms and 1 to 3 heteroatoms.

The term "substituted" refers to one or more substituents different from H, for example halogen; alkyl; aryl; heteroaryl, cycloalkyl; heterocyclyl; alkylene; alkynyl; OH; O-alkyl; O-alkylene; O-aryl; O-heteroaryl; $NH_2$; NH-alkyl; NH-aryl; NH-heteroaryl; N-alkyl-alkyl'; SH; S-alkyl; S-aryl; $S(O_2)H$; $S(O_2)$-alkyl; $S(O_2)$-aryl; $SO_3H$; $SO_3$-alkyl; $SO_3$-aryl; CHO; C(O)-alkyl; C(O)-aryl; C(O)OH; C(O)O-alkyl; C(O)O-aryl; OC(O)-alkyl; OC(O)-aryl; $C(O)NH_2$; C(O)NH-alkyl; C(O)NH-aryl; NHCHO; NHC(O)-alkyl; NHC(O)-aryl; NH-cycloalkyl; NH-heterocyclyl.

The subject of the present invention is also a method for preparing the products of formula (I).

The products according to the invention may be prepared from conventional methods of organic chemistry.

Schemes 1, 2, 3 and 4 below are illustrative of the methods used for the preparation of the examples relating to the substituted pyrroles. In this regard, they cannot constitute a limitation to the scope of the invention, as regards the methods for preparing the claimed compounds.

Scheme 1

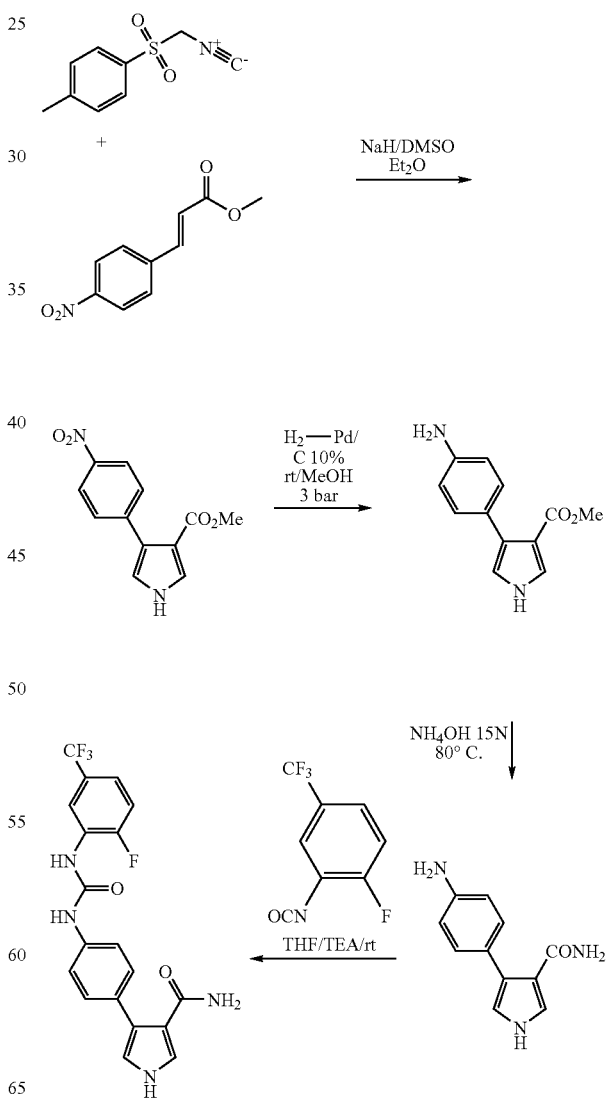

Scheme 2
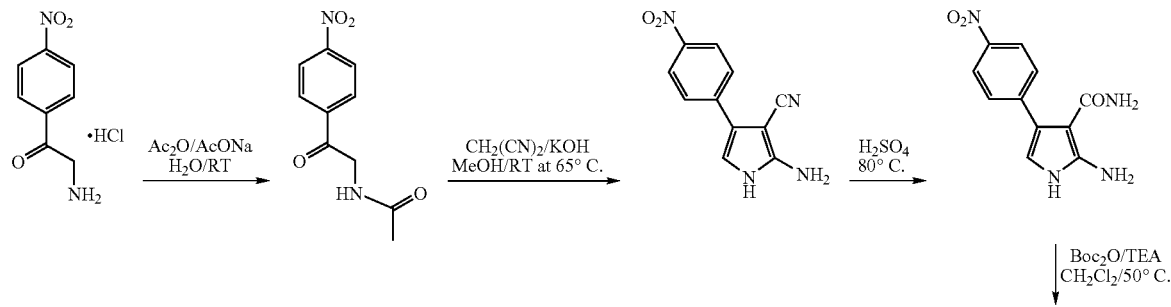
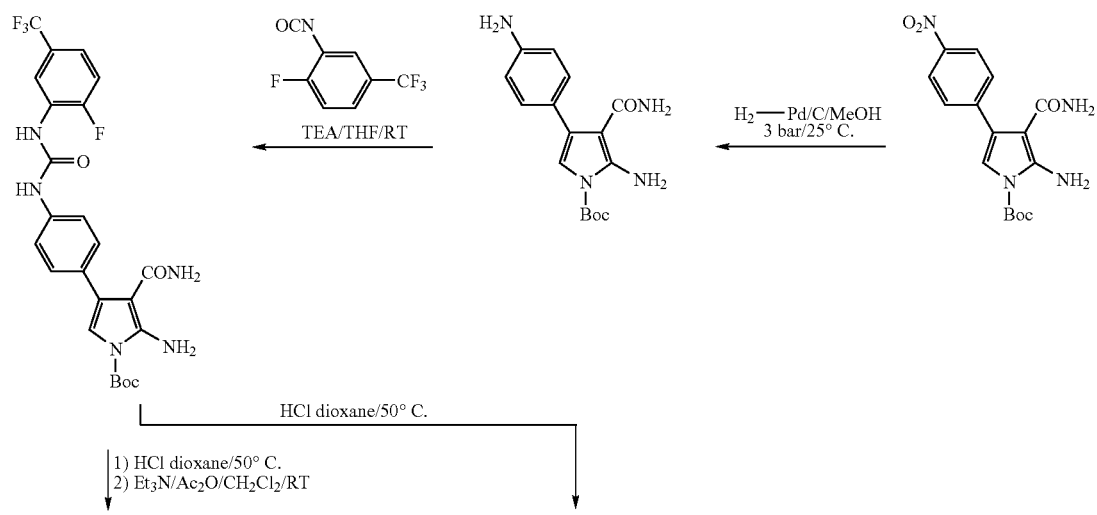
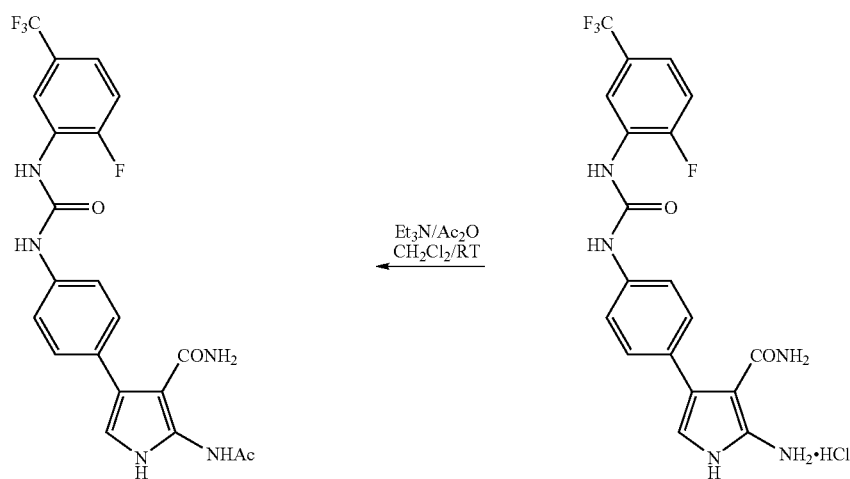

Scheme 3
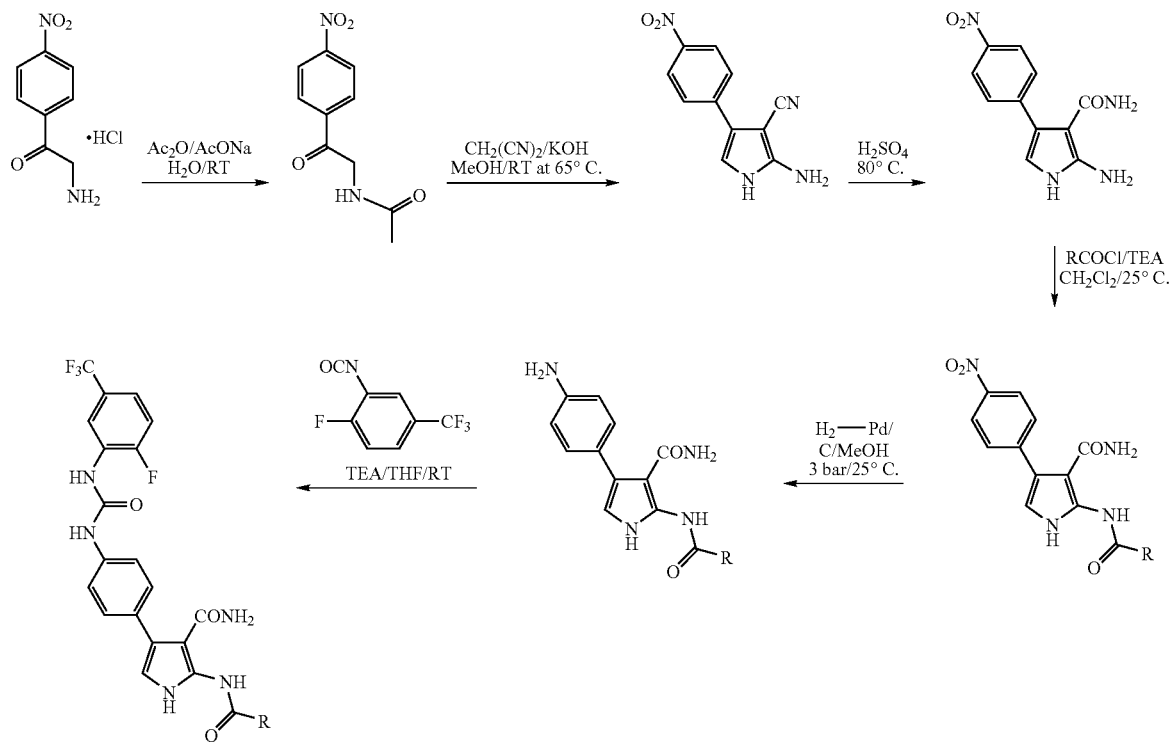
Scheme 4
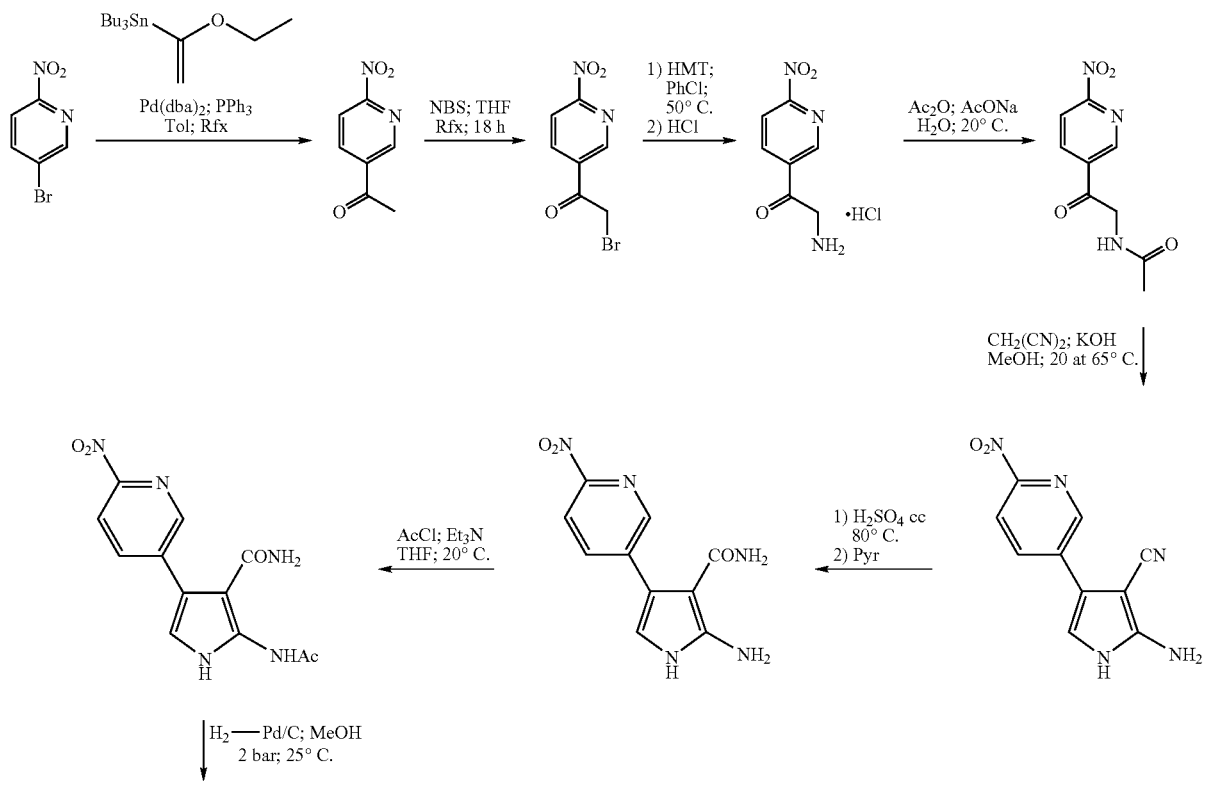

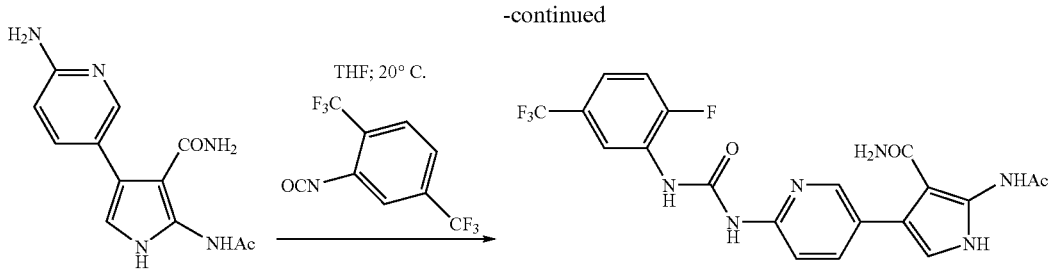

It is understood for persons skilled in the art that to carry out the methods according to the invention which are described above, it may be necessary to introduce groups protecting amino, carboxyl and alcohol functional groups in order to avoid side reactions. These groups are those which allow removal without affecting the remainder of the molecule. As examples of groups protecting the amino functional group, there may be mentioned tert-butyl carbamate which may be regenerated by means of trifluoroacetic acid or iodotrimethylsilane, acetyl which may be regenerated in an acidic medium (for example hydrochloric acid). As groups protecting the carboxyl functional group, esters (for example methoxymethyl ester, benzyl ester) may be mentioned. As groups protecting the alcohol functional group, there may be mentioned esters (for example benzoyl ester) which may be regenerated in an acidic medium or by catalytic hydrogenation. Other protecting groups which can be used are described by T. W. GREENE et al., in Protective Groups in Organic Synthesis, third edition, 1999, Wiley-Interscience.

The compounds of formula (I) are isolated and may be purified by the usual known methods, for example by crystallization, chromatography or extraction. The enantiomers and diastereoisomers of the compounds of formula (I) also form part of the invention.

The compounds of formula (I) containing a basic residue may be optionally converted to addition salts with an inorganic or organic acid, by the action of such an acid in a solvent, for example an organic solvent such as an alcohol, a ketone, an ether or a chlorinated solvent.

The compounds of formula (I) containing an acid residue may be optionally converted to metal salts or to addition salts with nitrogenous bases according to methods known per se. These salts may be obtained by the action of a metal (for example an alkali or alkaline earth metal) base, ammonia, an amine or an amine salt on a compound of formula (I), in a solvent. The salt formed is separated by the usual methods.

These salts also form part of the invention.

When a product according to the invention has at least one free basic functional group, pharmaceutically acceptable salts may be prepared by reaction between the said product and an inorganic or organic acid. Pharmaceutically acceptable salts include chlorides, nitrates, sulphates, hydrogen sulphates, pyrosulphates, bisulphates, sulphites, bisulphites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulphonates, p-toluenesulphonate, propanesulphonates, xylenesulphonates, salicylates, cinnamates, glutamates, aspartates, glucuronates, galacturonates.

When a product according to the invention has at least one free acid functional group, pharmaceutically acceptable salts may be prepared by reaction between the said product and an inorganic or organic base. Pharmaceutically acceptable bases include hydroxides of cations of alkali or alkaline-earth metals such as Li, Na, K, Mg, Ca, basic amine-containing compounds such as ammonia, arginine, histidine, piperidine, morpholine, piperazine, triethylamine.

The invention is also described by the following examples, given by way of illustration of the invention.

The LC/MS analyses were performed on a Micromass LCT model apparatus linked to a HP 1100 apparatus. The abundance of the products was measured with the aid of a HP G1315A diode array detector on a wave range of 200-600 nm and a light-scattering detector Sedex 65. The acquisition of the mass spectra was performed on a range from 180 to 800. The data were analysed using the Micromass MassLynx software. The separation was performed on a Hypersil BDS C18, 3 µm column (50×4.6 mm), eluting with a linear gradient from 5 to 90% acetonitrile containing 0.05% (v/v) of trifluoroacetic acid (TFA) in water containing 0.05% (v/v) TFA over 3.5 min at a flow rate of 1 ml/min. The total analysis time, including the period for re-equilibration of the column, is 7 min.

The MS spectra were performed in electrospray (ES$^+$) on a Platform II apparatus (Micromass). The principal ions observed are described.

The melting points were measured in a capillary, on a Mettler FP62 apparatus, range 30° C. to 300° C., rise of 2° C. per minute.

Purification by LC/MS:

The products may be purified by LC/MS using a Waters FractionsLynx system composed of a Waters model 600 gradient pump, a Waters model 515 regeneration pump, a Waters Reagent Manager dilution pump, a Waters model 2700 autoinjector, two Rheodyne model LabPro valves, a Waters model 996 diode array detector, a Waters model ZMD mass spectrometer and a Gilson model 204 fraction collector. The system was controlled by the Waters FractionLynx software. The separation was alternately performed on two Waters Symmetry columns (C$_{18}$, 5 µm, 19×50 mm, catalogue reference 186000210), one column being in the process of regeneration with a water/acetonitrile 95/5 (v/v) mixture containing 0.07% (v/v) trifluoroacetic acid, while the other column was in the process of separating. The elution of the columns was performed using a linear gradient of 5 to 95% acetonitrile containing 0.07% (v/v) of trifluoroacetic acid in water containing 0.07% (v/v) of trifluoroacetic acid, at a flow rate of 10 ml/min. At the outlet of the separating column, one-thousandth of the effluent is separated by an LC Packing Accurate, diluted with methyl alcohol at a flow rate of 0.5 ml/min and sent to the detectors, in an amount of 75% to the diode array detector, and the remaining 25% to the mass spectrometer. The remainder of the effluent (999/1000) is sent to the fraction collector where the stream is removed as long as the expected product mass is not detected by the FractionLynx software. The molecular formulae of the expected products are provided to the FractionLynx software which triggers the collection of the product when the mass signal detected corresponds to the ion [M+H]$^+$ and/or to [M+Na]$^+$. In some cases, depending on the analytical LC/MS results, when an intense ion corresponding to [M+2H]$^{++}$ was detected, the value corresponding to half of the calculated molecular mass (MW/2) is also provided to the FractionLynx software. Under these conditions, the collection is also triggered when the ion mass signal [M+2H]$^{++}$ and/or [M+Na+H]$^{++}$ are detected. The products were collected in a tarred glass tube. After collection, the solvents were evaporated in a Savant AES 2000 or Genevac HT8 centrifugal evaporator and the product masses were determined by weighing the tubes after evaporation of the solvents.

EI/CI analysis; direct introduction (DCI=sample deposition on a filament) Finnigan SSQ7000 mass spectrometer; mass domain m/z=29-900; electron energy 70 eV; source temperature 70° C.; reactant gas CI ammonia; EI=electron impact ionization; CI=chemical ionization.

Electrospray analysis; (positive electrospray: ES$^+$; negative electrospray: ES$^-$) LC-MS-DAD-ELSD coupling:

Method A

MS; Waters-Micromass Platform II; LC; Agilent HP 1100; Hypersil GOLD Thermo C18 column; 3×50 mm, 3 μm; eluent: water (with 0.1% formic acid)+acetonitrile gradient over 7 min; flow rate=0.8 ml/min; UV; DAD (λ=200-400 nm).

Method B

MS: Waters-Micromass QTOF-2; LC; Agilent HP 1100; Hypersil GOLD Thermo C18 column; 3×50 mm, 3 μm; eluent: water (with 0.1% formic acid)+acetonitrile gradient over 7 min; flow rate=0.9 ml/min; UV; DAD (λ=200-400 nm).

Method C

MS; Waters-Micromass ZQ; LC; Agilent HP 1100; XBRIDGE Waters C18 column; 3×50 mm, 2.5 μm; eluent: water (with 0.1% formic acid)+acetonitrile gradient of 7 min; flow rate=1.1 ml/min; UV; DAD (λ=254 nm).

$^1$H NMR spectrum at 400 MHz on a BRUKER AVANCE DRX-400 spectrometer or at 300 MHz on a BRUKER AVANCE DPX-300 spectrometer with the chemical shifts (δ in ppm)—in dimethyl sulphoxide solvent—d6 (DMSO-d6) referenced at 2.50 ppm at the temperature of 303 K.

EXAMPLE 1

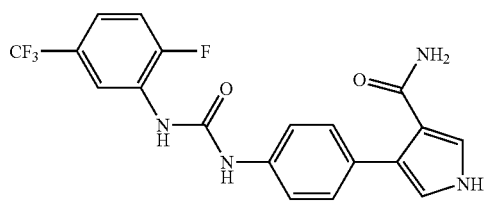

4-{4-[3-(2-Fluoro-5-trifluoromethylphenyl)ureido] phenyl}-1H-pyrrole-3-carboxamide 0.012 cm$^3$ of 2-fluoro-5-trifluoromethylphenyl isocyanate and 0.012 cm$^3$ of triethylamine are added at a temperature in the region of 20° C., under an argon atmosphere, to 0.017 g (84.48 mmol) of 4-(4-aminophenyl)-1H-pyrrole-3-carboxamide in suspension in 27 cm$^3$ of tetrahydrofuran. After stirring for 20 hours at a temperature in the region of 20° C., the reaction mixture is concentrated to dryness under reduced pressure (2.7 kPa) to give a residue which is purified by flash chromatography [eluent: ethyl acetate/dichloromethane (95/5 by volume)]. After concentrating the fractions under reduced pressure, a yellow residue is obtained which is stirred in 5 cm$^3$ of dichloromethane and then filtered and dried under reduced pressure (2.7 kPa) to give 22 mg of 4-{4-[3-(2-fluoro-5-trifluoromethylphenyl)-ureido]phenyl}-1H-pyrrole-3-carboxamide, in the form of a beige solid; $^1$H NMR (300 MHz, (CD$_3$)$_2$SO, —δ in ppm): from 6.57 to 7.02 (very broad m: 2H); 6.85 (broad t, J=2.5 Hz: 1H); 7.29 (broad t, J=2.5 Hz: 1H); from 7.33 to 7.43 (m; 5H); 7.49 (dd, J=10.5 and 8.5 Hz: 1H); 8.60 (dd, J=7.5 and 2.5 Hz: 1H); 9.31 (broad s: 1H); 9.58 (broad s: 1H); 11.2 (broad s: 1H); EI: m/z=406 (M$^+$), m/z=205 (C$_8$H$_3$NOF$_4$$^+$), m/z=179 (C$_7$H$_4$NF$_4$$^+$) base peak, ES+: m/z=407 (MH$^+$).

4-(4-Aminophenyl)-1H-pyrrole-3-carboxamide may be prepared in the following manner:

A suspension of 0.07 g (0.304 mmol) of ethyl 4-(4-aminophenyl)-1H-pyrrole-3-carboxylate in 10 cm$^3$ of a 22% aqueous ammonium hydroxide solution is heated in an autoclave at a temperature in the region of 80° C. for 84 hours. After stopping the heating and then returning to ambient temperature and pressure, the reaction mixture is concentrated to dryness under reduced pressure (2.7 kPa) to give an orange solid which is purified by flash chromatography [eluent: dichloromethane/methanol/acetonitrile (98/1/1 by volume)]. After concentrating the fractions under reduced pressure, a residue is obtained which is stirred in 10 cm$^3$ of diethyl ether and then filtered and dried under reduced pressure (2.7 kPa) to give 0.02 g of 4-(4-aminophenyl)-1H-pyrrole-3-carboxamide, in the form of a brown solid: EI: m/z=201 (M$^+$) base peak, m/z=185 (M–NH$_2$$^+$), m/z=157 (M-CONH$_2$$^+$).

Ethyl 4-(4-aminophenyl)-1H-pyrrole-3-carboxylate may be prepared in the following manner:

0.2 g (0.769 mmol) of ethyl 4-(4-nitrophenyl)-1H-pyrrole-3-carboxylate is added at a temperature in the region of 20° C. to a suspension of 0.02 g (0.188 mmol) of 10% palladium on carbon in 15 cm$^3$ of methanol. After hydrogenating for 20 hours in an autoclave under 3 bar of hydrogen, at a temperature in the region of 25° C., the reaction mixture is filtered, the catalyst is rinsed with three times 5 cm$^3$ of methanol and then the filtrate is concentrated to dryness under reduced pressure (2.7 kPa) to give a residue which is stirred in 10 cm$^3$ of diethyl ether and then filtered and dried under reduced pressure (2.7 kPa) to give 0.079 g of ethyl 4-(4-aminophenyl)-1H-pyrrole-3-carboxylate, in the form of a brown solid; EI: m/z=230 (M$^+$) base peak, m/z=202 (M-C$_2$H$_4$$^+$), m/z=157 (M-C$_2$H$_5$O$^+$).

Ethyl 4-(4-nitrophenyl)-1H-pyrrole-3-carboxylate may be prepared in the following manner:

A mixture of 2.212 g (10 mmol) of ethyl 4-nitrocinnamate and 1.991 g (10.2 mmol) of tosylmethyl isocyanate in solution in a mixture of 18 cm$^3$ of dimethyl sulphoxide and 36 cm$^3$ of diethyl ether is added dropwise, at a temperature in the region of 20° C., under an argon atmosphere, to a suspension of 0.512 g (12.8 mmol) of sodium hydride at 60% in mineral oil in 20 cm$^3$ of diethyl ether. After stirring for 1 hour under reflux, the reaction mixture is taken up in a mixture of 70 cm$^3$ of water, 20 cm$^3$ of a saturated aqueous sodium chloride solution and 100 cm$^3$ of ethyl acetate. The aqueous phase is extracted with 50 cm$^3$ of diethyl ether and twice 75 cm$^3$ of dichloromethane. All the organic phases are combined, dried over anhydrous sodium sulphate, filtered and concentrated to dryness under reduced pressure (2.7 kPa) to give a black oil which is taken up in a mixture of 75 cm³ of water and 50 cm³ of ethyl acetate. The aqueous phase is extracted with twice 50 cm³ of ethyl acetate. All the organic phases are combined, dried over anhydrous sodium sulphate, filtered and concentrated to dryness under reduced pressure (2.7 kPa) to give 2.82 g of a black solid which is purified by flash chromatography [eluent: cyclohexane/ethyl acetate (3/2 by volume)]. After concentrating the fractions under reduced pressure, 1.48 g of an orange solid are obtained, which solid is purified by flash chromatography [eluent: dichiloromethane]. After concentrating the fractions under reduced pressure, 0.78 g of ethyl 4-(4-nitrophenyl)-1H-pyrrole-3-carboxylate is obtained, in the form of a yellow solid; EI: m/z=260 (M$^+$) base peak, m/z=215 (M-C$_2$H$_5$O$^+$), m/z=169 (215-NO$_2$).

EXAMPLE 2

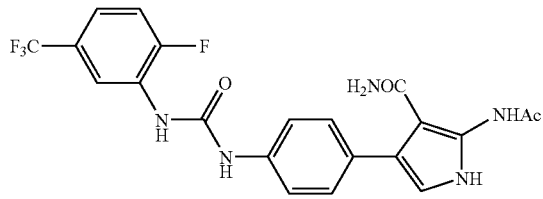

1-Acetyl-2-amino-4-{4-[3-(2-fluoro-5-trifluoromethylphenyl)ureido]phenyl}-1H-pyrrole-3-carboxamide 0.575 cm³ of a 4M hydrochloric acid solution in dioxane is added at a temperature in the region of 20° C., under an argon atmosphere, to 0.06 g (0.115 mmol) of tert-butyl 2-amino-3-carbamoyl-4-{4-[3-(2-fluoro-5-trifluoromethylphenyl)ureido]phenyl}pyrrole-1-carboxylate in solution in a mixture of 1.2 cm³ of dioxane and 1.2 cm³ of methanol. After stirring for 15 hours at a temperature in the region of 50° C., the reaction mixture is concentrated to dryness under reduced pressure (2.7 kPa) to give 2-amino-3-carbamoyl-4-{4-[3-(2-fluoro-5-trifluoromethylphenyl)ureido]phenyl}-1H-pyrrole hydrochloride which is taken up in 2.5 cm³ of ethyl acetate. 0.01 cm³ of triethylamine and 0.013 cm³ of acetic anhydride are added at a temperature in the region of 20° C., under an argon atmosphere. After stirring for 1 hour at a temperature in the region of 20° C., a catalytic quantity of DMAP is added and then the stirring is maintained for 30 minutes. The reaction mixture is diluted with 5 cm³ of ethyl acetate. The organic phase is washed with twice 5 cm³ of water. All the aqueous phases are combined and extracted with 5 cm³ of ethyl acetate. All the organic phases are combined, washed with 5 cm³ of a saturated aqueous sodium chloride solution, dried over anhydrous magnesium sulphate, filtered and concentrated to dryness under reduced pressure (2.7 kPa) to give 0.054 g of a residue which is purified by flash chromatography [eluent: dichloromethane/methanol (98/2 by volume)]. After concentrating the fractions under reduced pressure, 0.010 g of 1-acetyl-2-amino-4-{4-[3-(2-fluoro-5-trifluoromethylphenyl)ureido]phenyl}-1H-pyrrole-3-carboxamide is obtained, in the form of a yellow solid; ¹H NMR (300 MHz, (CD$_3$)$_2$SO, —δ in ppm): 2.14 (s: 3H); from 5.20 to 6.10 (broad m: 1H); 6.40 (d, J=2.0 Hz: 1H); from 6.70 to 7.60 (broad m: 1H); 7.30 (broad d, J=8.5 Hz: 2H); 7.38 (mt: 1H); from 7.45 to 7.54 (m: 3H); 8.62 (dd, J=7.5 and 2.5 Hz: 1H); 8.92 (broad s: 1H); 9.25 (broad s: 1H); 10.7 (broad s: 1H); 11.4 (broad s: 1H); ES+: m/z=464 (MH$^+$).

tert-Butyl 2-amino-3-carbamoyl-4-{4-[3-(2-fluoro-5-trifluoromethylphenyl)-ureido]phenyl}pyrrole-1-carboxylate may be prepared in the following manner: 0.125 cm³ of triethylamine and 0.049 cm³ of 2-fluoro-5-trifluoromethylphenyl isocyanate are added at a temperature in the region of 20° C., under an argon atmosphere, to 0.07 g (0.221 mmol) of tert-butyl 2-amino-4-(4-aminophenyl)-3-carbamoylpyrrole-1-carboxylate in solution in 2 cm³ of tetrahydrofuran. After stirring for 4 hours at a temperature in the region of 20° C., the reaction mixture is taken up in 5 cm³ of dichloromethane. The organic phase is washed with twice 5 cm³ of water. All the aqueous phases are combined and extracted with 5 cm³ of dichloromethane. All the organic phases are combined, washed with 5 cm³ of a saturated aqueous sodium chloride solution, dried over anhydrous magnesium sulphate, filtered and concentrated to dryness under reduced pressure (2.7 kPa) to give 0.135 g of an orange solid which is purified by flash chromatography [eluent: dichloromethane/methanol (100/0 to 98/2 by volume)]. After concentrating the fractions under reduced pressure, 0.077 g of tert-butyl 2-amino-3-carbamoyl-4-{4-[3-(2-fluoro-5-trifluoromethylphenyl)-ureido]phenyl}pyrrole-1-carboxylate is obtained, in the form of a yellow solid; ES+: m/z=522 (MH$^+$).

tert-Butyl 2-amino-4-(4-aminophenyl)-3-carbamoylpyrrole-1-carboxylate may be prepared in the following manner: 0.075 g (0.216 mmol) of tert-butyl 2-amino-3-carbamoyl-4-(4-nitrophenyl)-pyrrole-1-carboxylate is added at a temperature in the region of 25° C. to a suspension of 0.008 g (0.0076 mmol) of 10% palladium on carbon in 12 cm³ of methanol. After hydrogenating for 17 hours in an autoclave under 3 bar of hydrogen, at a temperature in the region of 25° C., the reaction mixture is filtered, the catalyst is rinsed with three times 5 cm³ of methanol and then the filtrate is concentrated to dryness under reduced pressure (2.7 kPa) to give 0.072 g of tert-butyl 2-amino-4-(4-aminophenyl)-3-carbamoylpyrrole-1-carboxylate, in the form of a yellow solid; ¹H NMR (400 MHz, (CD$_3$)$_2$SO, —δ in ppm); 1.55 (s: 9H); from 4.80 to 5.35 (very broad m: 1H); 5.22 (broad s 2H); 6.32 (s: 1H); from 6.40 to 6.85 (very broad m: 1H); 6.60 (broad d, J=8.5 Hz: 2H); 6.99 (broad d, J=8.5 Hz: 2H); 7.01 (broad s: 2H).

tert-Butyl 2-amino-3-carbamoyl-4-(4-nitrophenyl)pyrrole-1-carboxylate may be prepared in the following manner:

0.075 cm³ (0.536 mmol) of triethylamine and then 0.117 g (0.536 mmol) of di-tert-butyl dicarbonate are added at a temperature in the region of 20° C., under an argon atmosphere, to 0.11 g (0.447 mmol) of 2-amino-4-(4-nitrophenyl)-1H-pyrrole-3-carboxamide in suspension in 6 cm³ of dichloromethane. After stirring for 2.5 hours at a temperature in the region of 50° C., 0.09 g (0.412 mmol) of di-tert-butyl dicarbonate is added and the stirring is maintained at a temperature in the region of 50° C. for 3 hours. The reaction mixture is taken up in 5 cm³ of dichloromethane. The organic phase is washed with three times 5 cm³ of water. All the aqueous phases are combined and extracted with 5 cm³ of dichloromethane. All the organic phases are combined, dried over anhydrous magnesium sulphate, filtered and concentrated to dryness under reduced pressure (2.7 kPa) to give 0.28 g of a residue which is purified by flash chromatography [eluent: dichloromethane]. After concentrating the fractions under reduced pressure, 0.075 g of tert-butyl 2-amino-3-carbamoyl- 4-(4-nitrophenyl)pyrrole-1-carboxylate is obtained, in the form of an orange solid; $^1$H NMR (300 MHz, (CD$_3$)$_2$SO, —δ in ppm): 1.57 (s; 9H); from 5.77 to 6.58 (broad m: 2H); 6.72 (s: 1H); 6.93 (broad s: 2H); 7.63 (broad d, J=8.5 Hz: 2H); 8.23 (broad d, J=8.5 Hz: 2H).

2-Amino-4-(4-nitrophenyl)-1H-pyrrole-3-carboxamide may be prepared in the following manner:

A suspension of 0.26 g (1.139 mmol) of 2-amino-4-(4-nitrophenyl)-1H-pyrrole-3-carbonitrile in 5 cm$^3$ of concentrated sulphuric acid is heated at a temperature in the region of 80° C. for 1 hour. After having cooled the reaction mixture to a temperature in the region of 20° C., it is poured over crushed ice and then a 5N aqueous sodium hydroxide solution is slowly added to a basic pH in the region of 10. The reaction mixture is extracted with 7 times 10 cm$^3$ of a dichloromethane/MeOH mixture (98/2 by volume). All the organic phases are combined, dried over anhydrous magnesium sulphate, filtered and concentrated to dryness under reduced pressure (2.7 kPa) to give 0.19 g of 2-amino-4-(4-nitrophenyl)-1H-pyrrole-3-carboxamide, in the form of a red-brown solid; EI: m/z=246 (M$^+$) base peak, m/z=229 (M–NH$_3$$^+$).

2-Amino-4-(4-nitrophenyl)-1H-pyrrole-3-carbonitrile may be prepared in the following manner:

0.223 g (3.375 mmol) of malononitrile is added at a temperature in the region of 20° C., under an argon atmosphere, to 0.5 g (2.25 mmol) of N-[2-(4-nitro-phenyl)-2-oxoethyl] acetamide in solution in 15 cm$^3$ of methanol. The reaction medium is cooled to a temperature in the region of 0° C. and then 0.5 cm$^3$ of a 50% aqueous potassium hydroxide solution is added. After stirring for 15 minutes at a temperature in the region of 0° C. and then for 30 minutes at a temperature in the region of 65° C., the reaction mixture is cooled to a temperature in the region of 20° C. and then poured over crushed ice and extracted with seven times 10 cm$^3$ of dichloromethane. All the organic phases are combined, washed with 50 cm$^3$ of a saturated aqueous sodium chloride solution, dried over anhydrous magnesium sulphate, filtered and concentrated to dryness under reduced pressure (2.7 kPa) to give 0.7 g of a brown solid which is purified by flash chromatography [eluent: dichloromethane/methanol (100/0 to 95/5 by volume)]. After concentrating the fractions under reduced pressure, 0.265 g of 2-amino-4-(4-nitrophenyl)-1H-pyrrole-3-carbonitrile is obtained, in the form of a brown solid; EI: m/z=228 (M$^+$) base peak, m/z 182 (M-NO$_2$).

N-[2-(4-Nitrophenyl)-2-oxoethyl]acetamide may be prepared in the following manner:

0.435 cm$^3$ (4.616 mmol) of acetic anhydride and then 0.379 g (4.616 mmol) of sodium acetate in solution in 1.5 cm$^3$ of water are added at a temperature in the region of 0° C., under an argon atmosphere, to 0.5 g (2.308 mmol) of 2-amino-(4-nitrophenyl)acetophenone in suspension in 2 cm$^3$ of water. After having left the temperature to vary between 0° C. and 20° C. for 1 hour, 1.5 cm$^3$ of concentrated hydrochloric acid are added to a pH=2. The reaction mixture is extracted with five times 10 cm$^3$ of dichloromethane. All the organic phases are combined, dried on anhydrous magnesium sulphate, filtered and concentrated to dryness under reduced pressure (2.7 kPa) to give 0.37 g of N-[2-(4-nitrophenyl)-2-oxoethyl]acetamide, in the form of a yellow solid; ES+: m/z=223 (MH$^+$).

EXAMPLE 3

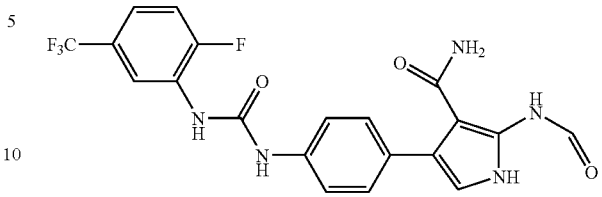

2-Formylamino-4-{4-[3-(2-fluoro-5-trifluoromethylphenyl)ureido]phenyl}-1H-pyrrole-3-carboxamide 0.081 cm$^3$ of triethylamine and 0.084 cm$^3$ of 2-fluoro-5-trifiloromethylphenyl isocyanate is added at a temperature in the region of 23° C. to 0.125 g (0.578 mmol) of 2-formylamino-4-(4-aminophenyl)-1H-pyrrole-3-carboxamide in solution in 15 cm$^3$ of tetrahydrofuran. After stirring for 16 hours at a temperature in the region of 23° C., the reaction mixture is concentrated to dryness under reduced pressure (2.7 kPa). The residue is then diluted in 50 cm$^3$ of ethyl acetate and then washed with twice 50 cm$^3$ of water and 50 cm$^3$ of a saturated aqueous sodium chloride solution. The organic solution is dried over anhydrous magnesium sulphate and treated with 3S black, filtered and concentrated to dryness under reduced pressure (2.7 kPa) to give 0.115 g of an oily solid which is purified by flash chromatography [eluent: dichloromethane/methanol/acetonitrile (95/2.5/2.5 by volume)]. After concentrating the fractions under reduced pressure, 0.016 g of 2-formylamino-4-{4-[3-(2-fluoro-5-trifluoromethylphenyl)ureido]phenyl}-1H-pyrrole-3-carboxamide is obtained in the form of a cream solid melting at 169° C. $^1$H NMR (400 MHz, (CD$_3$)$_2$SO, —δ in ppm) 5.60 (broad m, 1H); 6.41 (broad s, 1H); 7.07 (broad m, 1H); 7.31 (d, J=8.5 Hz, 2H); 7.38 (m, 1H); 7.48 (m partially masked, 1H); 7.51 (d, J=8.5 Hz, 2H); 8.34 (s, 1H); 8.61 (dd, J=2.5 and 7.5 Hz, 1H); 9.07 (broad s, 1H); 9.40 (broad s, 1H); 10.85 (broad m, 1H); 11.45 (broad s, 1H).

2-Formylamino-4-(4-aminophenyl)-1H-pyrrole-3-carboxamide may be prepared in the following manner:

0.23 g (0.834 mmol) of 2-formylamino-4-(4-nitrophenyl)-1H-pyrrole-3-carboxamide is added at a temperature in the region of 25° C. to a suspension of 0.030 g (0.0285 mmol) of 10% palladium on carbon in 15 cm$^3$ of methanol. After hydrogenation for 5 hours in an autoclave under 2 bar of hydrogen, at a temperature in the region of 25° C., the reaction mixture is filtered, the catalyst is rinsed with three times 5 cm$^3$ of methanol and then the filtrate is concentrated to dryness under reduced pressure (2.7 kPa) to give 0.125 g of 2-formylamino-4-(4-aminophenyl)-1H-pyrrole-3-carboxamide, in the form of a green solid. $^1$H NMR (400 MHz, (CD$_3$)$_2$SO, —δ in ppm) 5.13 (broad s, 2H); 5.43 (broad m, 1H); 6.27 (d, J=2.5 Hz, 1H); 6.60 (d, J=9.0 Hz, 2H); 6.80 (broad m, 1H); 6.99 (d, J=9.0 Hz, 2H); 8.34 (d, J=1.5 Hz, 1H); 10.9 (broad s, 1H); 11.25 (broad s, 1H)

2-Formylamino-4-(4-nitrophenyl)-1H-pyrrole-3-carboxamide may be prepared in the following manner:

A solution of 2 cm$^3$ (52.9 mmol) of formic acid in 5 cm$^3$ (52.9 mmol) of acetic anhydride is added, at a temperature close to 25° C., to a solution of 0.3 g (1.21 mmol) of 2-amino-4-(4-nitrophenyl)-1H-pyrrole-3-carboxamide in 5 cm$^3$ of absolute ethanol. After stirring for 2 hours at this temperature, the reaction medium is poured into 100 cm$^3$ of water. The suspension is then filtered. The solid is drained, dried to give 0.257 g of 2-formylamino-4-(4-nitrophenyl)-1H-pyrrole-3-carboxamide in the form of a green powder. $^1$H NMR (400 MHz, (CD$_3$)$_2$SO, —δ in ppm), from 6.22 to 8.53 (very broad m, 2H); 6.78 (d, J=3.0 Hz, 1H); 7.64 (d, J=9.0 Hz, 2H); 8.19 (d, J=9.0 Hz, 2H); 8.32 (d, J=1.5 Hz, 1H); 10.55 (broad s, 1H); 11.6 (broad s, 1H).

2-Amino-4-(4-nitrophenyl)-1H-pyrrole-3-carboxamide is prepared as described in Example 2:

EXAMPLE 4

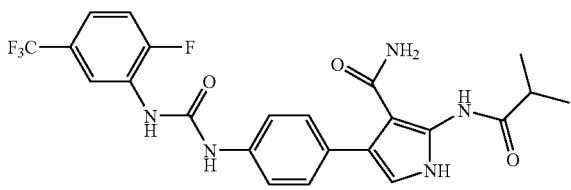

2-Isobutyrylamino-4-{4-[3-(2-fluoro-5-trifluoromethylphenyl)ureido]phenyl}-1H-pyrrole-3-carboxamide 0.076 cm$^3$ (0.436 mmol) of 2-fluoro-5-trifluoromethylphenyl isocyanate is added at a temperature in the region of 25° C. to 0.125 g (0.436 mmol) of 2-isobutyrylamino-4-(4-aminophenyl)-1H-pyrrole-3-carboxamide in solution in 15 cm$^3$ of tetrahydrofuran. After stirring for 17 hours at a temperature in the region of 25° C., the reaction mixture is concentrated to dryness under reduced pressure (2.7 kPa). The residue is then diluted in 40 cm$^3$ of ethyl acetate and then washed with 40 cm$^3$ of water. The organic solution is dried over anhydrous magnesium sulphate, filtered and concentrated to dryness under reduced pressure (2.7 kPa) to give a residue which is crystallized from 8 cm$^3$ of a cyclohexane/ethyl acetate mixture (70/30 by volume). After filtration and drying, 0.096 g of 2-isobutyrylamino-4-{4-[3-(2-fluoro-5-trifluoromethylphenyl)-ureido]phenyl}-1H-pyrrole-3-carboxamide is obtained in the form of a cream solid melting at 196° C. IR (KBr), 3472; 3384; 1667; 1594; 1546; 1443; 1340; 1313; 1198; 1167; 1120; 1070; 937 & 614 cm$^{-1}$. $^1$H NMR (400 MHz, (CD$_3$)$_2$SO, —δ in ppm), 1.17 (d, J=7.0 Hz, 6H); 2.61 (m, 1H); 5.62 (broad m, 1H); 6.40 (d, J=2.5 Hz, 1H); 7.00 (broad m, 1H); 7.30 (d, J=9.0 Hz, 2H); 7.39 (m, 1H); 7.49 (m partially masked, 1H); 7.51 (d, J=9.0 Hz, 2H); 8.62 (dd, J=2.5 and 7.5 Hz, 1H); 8.99 (broad s, 1H); 9.32 (broad s, 1H); 10.95 (broad s, 1H); 11.45 (broad s, 1H).

2-Isobutyrylamino-4-(4-aminophenyl)-1H-pyrrole-3-carboxamide may be prepared in the following manner:

0.33 g (1.04 mmol) of 2-isobutyrylamino-4-(4-nitrophenyl)-1H-pyrrole-3-carboxamide is added at a temperature in the region of 25° C. to a suspension of 0.047 g (0.0446 mmol) of 10% palladium on carbon in 25 cm$^3$ of methanol. After hydrogenating for 3.5 hours in an autoclave under 2 bar of hydrogen, at a temperature in the region of 25° C., the reaction mixture is filtered, the catalyst is rinsed with three times 5 cm$^3$ of methanol and then the filtrate is concentrated to dryness under reduced pressure (2.7 kPa) to give 0.22 g of a residue which is purified by flash chromatography [eluent: dichloromethane/methanol/acetonitrile (96/2/2 by volume)]. After concentrating the fractions under reduced pressure, 0.135 g of 2-isobutyrylamino-4-(4-aminophenyl)-1H-pyrrole-3-carboxamide is obtained, in the form of a brown solid. $^1$H NMR (400 MHz, (CD$_3$)$_2$SO, —δ in ppm) 1.16 (d, J=7.0 Hz, 6H); 2.60 (m, 1H); 5.15 (broad s, 2H); 5.45 (broad m, 1H); 6.24 (d, J=2.0 Hz, 1H); 6.60 (d, J=9.0 Hz, 2H); 6.94 (broad m, 1H); 6.98 (d, J=9.0 Hz, 2H); 11.05 (broad s, 1H); 11.3 (broad s, 1H).

2-Isobutyrylamino-4-(4-nitrophenyl)-1H-pyrrole-3-carboxamide may be prepared in the following manner:

0.260 cm$^3$ (1.86 mmol) of triethylamine and 0.098 cm$^3$ (0.93 mmol) of isobutyryl chloride are added, at a temperature close to 25° C., to a solution of 0.23 g (0.93 mmol) of 2-amino-4-(4-nitrophenyl)-1H-pyrrole-3-carboxamide in 15 cm$^3$ of tetrahydrofuran. After stirring for 16 hours at this temperature, the reaction medium is concentrated to dryness under reduced pressure (2.7 kPa) to give a residue which is stirred in 60 cm$^3$ of water and then extracted with twice 50 cm$^3$ of ethyl acetate. The organic phase is dried over anhydrous magnesium sulphate, filtered and concentrated to dryness under reduced pressure (2.7 kPa) to give 0.35 g of 2-isobutyrylamino-4-(4-nitro-phenyl)-1H-pyrrole-3-carboxamide in the form of a green powder. $^1$H NMR (400 MHz, (CD$_3$)$_2$SO, —δ in ppm) 15 (d, J=7.0 Hz, 6H); 2.64 (m, 1H); from 6.50 to 8.50 (very broad m, 2H); 6.79 (d, J=2.5 Hz, 1H); 7.64 (d, J=9.0 Hz, 2H); 8.19 (d, J=9.0 Hz, 2H); 10.45 (broad s, 1H); 11.65 (broad s, 1H).

2-Amino-4-(4-nitrophenyl)-1H-pyrrole-3-carboxamide is prepared as described in Example 2.

EXAMPLE 5

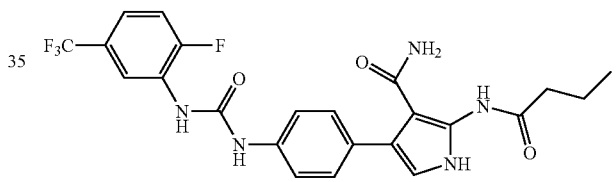

2-Butyrylamino-4-{4-[3-(2-fluoro-5-trifluoromethylphenyl)ureido]phenyl}-1H-pyrrole-3-carboxamide:

0.096 cm$^3$ (0.671 mmol) of 2-fluoro-5-trifluoromethylphenyl isocyanate is added at a temperature in the region of 25° C. to 0.207 g (0.610 mmol) of 2-butyrylamino-4-(4-aminophenyl)-1H-pyrrole-3-carboxamide in solution in 20 cm$^3$ of tetrahydrofuran. After stirring for 48 hours at a temperature in the region of 25° C., the reaction mixture is concentrated to dryness under reduced pressure (2.7 kPa). The residue is then diluted in 40 cm$^3$ of ethyl acetate and then washed with twice 30 cm$^3$ of water and 30 cm$^3$ of a saturated aqueous sodium chloride solution. The organic solution is dried over anhydrous magnesium sulphate, filtered and concentrated to dryness under reduced pressure (2.7 kPa) to give a residue which is purified by flash chromatography [eluent: dichloromethane/methanol/acetonitrile (97/1.5/1.5 by volume)]. After concentrating the fractions under reduced pressure, 0.093 g of 2-butyryl-amino-4-{4-[3-(2-fluoro-5-trifluoromethylphenyl)ureido]phenyl}-1H-pyrrole-3-carboxamide is obtained in the form of a cream solid melting at 219° C. IR (KBr), 3470; 3387; 1717; 1626; 1593; 1546; 1443; 1341; 1315; 1264; 1193; 1168; 1126; 1070; 820; 614 cm$^{-1}$. $^1$H NMR (400 MHz, (CD$_3$)$_2$SO, —δ in ppm) 0.95 (t, J=7.5 Hz, 3H); 1.64 (m, 2H); 2.38 (t, J=7.5 Hz, 2H); 5.60 (broad m, 1H); 6.39 (d, J=2.5 Hz, 1H); 7.05 (broad m, 1H); 7.30 (d, J=9.0 Hz, 2H); 7.38 (m, 1H); 7.49 (m partially masked, 1H); 7.51 (d, J=9.0 Hz, 2H); 8.61 (dd, J=2.5 and 7.5 Hz, 1H); 9.05 (broad s, 1H); 9.38 (broad s, 1H); 10.8 (broad s, 1H); 11.4 (broad s, 1H).

2-Butyrylamino-4-(4-aminophenyl)-1H-pyrrole-3-carboxamide may be prepared in the following manner:

0.195 g (0.61 mmol) of 2-butyrylamino-4-(4-nitrophenyl)-1H-pyrrole-3-carboxamide is added at a temperature in the region of 25° C. to a suspension of 0.068 g (0.064 mmol) of 10% palladium on carbon in 20 cm³ of methanol. After hydrogenating for 5 hours in an autoclave under 2 bar of hydrogen, at a temperature in the region of 25° C., the reaction mixture is filtered, the catalyst is rinsed with twice 10 cm³ of methanol and then the filtrate is concentrated to dryness under reduced pressure (2.7 kPa) to give 0.207 g of 2-butyrylamino-4-(4-aminophenyl)-1H-pyrrole-3-carboxamide, in the form of a cream solid. ¹H NMR (400 MHz, (CD₃)₂SO, —δ in ppm) 0.94 (t, J=7.5 Hz, 3H); 1.63 (m, 2H); 2.37 (t, J=7.5 Hz, 2H); 5.11 (broad s, 2H); from 6.05 to 8.45 (very broad m, 2H); 6.24 (d, J=2.5 Hz, 1H); 6.60 (d, J=8.5 Hz, 2H); 6.99 (d, J=8.5 Hz, 2H); 10.8 (broad s, 1H); 11.3 (broad s, 1H).

2-Butyrylamino-4-(4-nitrophenyl)-1H-pyrrole-3-carboxamide may be prepared in the following manner:

0.227 cm³ (1.62 mmol) of triethylamine and 0.085 cm³ (0.81 mmol) of butyryl chloride are added, at a temperature close to 25° C., to a solution of 0.20 g (0.81 mmol) of 2-amino-4-(4-nitro-phenyl)-1H-pyrrole-3-carboxamide in 25 cm³ of tetrahydrofuran. After stirring for 16 hours at this temperature, the reaction medium is concentrated to dryness under reduced pressure (2.7 kPa) to give a residue which is stirred in 60 cm³ of ethyl acetate and then washed with three times 20 cm³ of water. The organic phase is dried over anhydrous magnesium sulphate, filtered and concentrated to dryness under reduced pressure (2.7 kPa) to give 0.221 g of 2-butyrylamino-4-(4-nitrophenyl)-1H-pyrrole-3-carboxamide in the form of a brown powder. ¹H NMR (400 MHz, (CD₃)₂SO, —δ in ppm) 0.94 (t, J=7.5 Hz, 3H); 1.63 (m, 2H); 2.36 (t, J=7.5 Hz, 2H); from 6.20 to 8.50 (very broad m, 2H); 6.79 (d, J=3.0 Hz, 1H); 7.64 (d, J=9.0 Hz, 2H); 8.18 (d, J=9.0 Hz, 2H); 10.3 (broad s, 1H); 11.6 (broad s, 1H).

2-Amino-4-(4-nitrophenyl)-1H-pyrrole-3-carboxamide is prepared as described in Example 2.

EXAMPLE 6

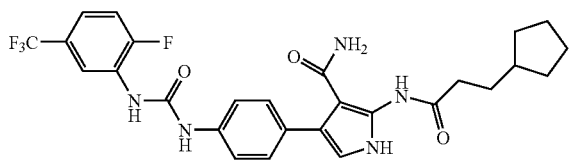

2-(3-Cyclopentylpropionylamino)-4-{4-[3-(2-fluoro-5-trifluoromethylphenyl)-ureido]phenyl}-1H-pyrrole-3-carboxamide 0.072 cm³ (0.50 mmol) of 2-fluoro-5-trifluoromethylphenyl isocyanate is added at a temperature in the region of 25° C. to 0.170 g (0.50 mmol) of 2-(3-cyclo-pentylpropionylamino)-4-(4-aminophenyl)-1H-pyrrole-3-carboxamide in solution in 20 cm³ of tetrahydrofuran. After stirring for 48 hours at a temperature in the region of 25° C., the reaction mixture is concentrated to dryness under reduced pressure (2.7 kPa). The residue is then diluted in 50 cm³ of ethyl acetate and then washed with 50 cm³ of water and 50 cm³ of a saturated aqueous sodium chloride solution. The organic solution is dried over anhydrous magnesium sulphate, filtered and concentrated to dryness under reduced pressure (2.7 kPa) to give a residue which is purified by flash chromatography [eluent; dichloromethane/methanol/acetonitrile (95/2.5/2.5 by volume)]. After concentrating the fractions under reduced pressure, 0.048 g of 2-(3-cyclopentylpropionylamino)-4-{4-[3-(2-fluoro-5-trifluoromethylphenyl)-ureido]phenyl}-1H-pyrrole-3-carboxamide is obtained in the form of a yellow powder melting at 222° C. IR (KBr), 3470; 3389; 1717; 1633; 1594; 1546; 1443; 1341; 1312; 1194; 1167; 1119; 1070 & 614 cm⁻¹. ¹H NMR (400 MHz, (CD₃)₂SO, —δ in ppm) 1.11 (m, 2H); from 1.42 to 1.68 (m, 6H); from 1.71 to 1.85 (m, 3H); 2.40 (t, J=8.0 Hz, 2H); 5.56 (broad m, 1H); 6.39 (d, J=2.5 Hz, 1H); 7.09 (broad m, 1H); 7.30 (d, J=9.0 Hz, 2H); 7.38 (m, 1H); 7.49 (m partially masked, 1H); 7.51 (d, J=9.0 Hz, 2H); 8.62 (dd, J=2.5 and 7.5 Hz, 1H); 9.00 (broad s, 1H); 9.32 (broad s, 1H); 10.8 (broad s, 1H); 11.4 (broad s, 1H).

2-(3-Cyclopentylpropionylamino)-4-(4-aminophenyl)-1H-pyrrole-3-carboxamide is prepared in the following manner:

0.210 g (0.56 mmol) of 2-(3-cyclopentylpropionylamino)-4-(4-nitrophenyl)-1H-pyrrole-3-carboxamide is added at a temperature in the region of 25° C. to a suspension of 0.055 g (0.0051 mmol) of 10% palladium on carbon in 25 cm³ of methanol. After hydrogenating for 5 hours in an autoclave under 2 bar of hydrogen, at a temperature in the region of 25° C., the reaction mixture is filtered, the catalyst is rinsed with twice 10 cm³ of methanol and then the filtrate is concentrated to dryness under reduced pressure (2.7 kPa) to give 0.151 g of 2-(3-cyclopentylpropionylamino)-4-(4-aminophenyl)-1H-pyrrole-3-carboxamide, in the form of a brown powder. ¹H NMR (400 MHz, (CD₃)₂SO, —δ in ppm) 1.09 (m, 2H); from 1.39 to 1.84 (m, 9H); 2.39 (t, J=8.0 Hz, 2H); 5.14 (broad s, 2H); from 6.20 to 7.50 (very broad m, 2H); 6.23 (d, J=2.5 Hz, 1H); 6.59 (d, J=8.5 Hz, 2H); 6.99 (d, J=8.5 Hz, 2H); 10.9 (broad s, 1H); 11.3 (broad s, 1H).

2-(3-Cyclopentylpropionylamino)-4-(4-nitrophenyl)-1H-pyrrole-3-carboxamide may be prepared in the following manner:

0.171 cm³ (1.22 mmol) of triethylamine and 0.098 mg (0.61 mmol) of 3-cyclopentylpropionyl chloride are added, at a temperature close to 25° C., to a solution of 0.15 g (0.61 mmol) of 2-amino-4-(4-nitrophenyl)-1H-pyrrole-3-carboxamide in 25 cm³ of tetrahydrofuran. After stirring for 16 hours at this temperature, the reaction medium is concentrated to dryness under reduced pressure (2.7 kPa) to give a residue which is stirred in 40 cm³ of water and then extracted with three times 40 cm³ of ethyl acetate. The organic phase is washed with 80 cm³ of a saturated aqueous sodium chloride solution, dried over anhydrous magnesium sulphate, filtered and concentrated to dryness under reduced pressure (2.7 kPa) to give 0.218 g of 2-(3-cyclopentyl-propionylamino)-4-(4-nitrophenyl)-1H-pyrrole-3-carboxamide in the form of a green powder. ¹H NMR (400 MHz, (CD₃)₂SO, —δ in ppm) 1.11 (m, 2H); from 1.42 to 1.65 (m, 6H); from 1.69 to 1.86 (m, 3H); 2.39 (t, J=8.0 Hz, 2H); from 6.17 to 8.50 (very broad m, 2H); 6.79 (d, J=2.5 Hz, 1H); 7.63 (d, J=9.0 Hz, 2H); 8.18 (d, J=9.0 Hz, 2H); 10.35 (broad s, 1H); 11.6 (broad s, 1H)

2-Amino-4-(4-nitrophenyl)-1H-pyrrole-3-carboxamide is prepared as described in Example 2.

EXAMPLE 7

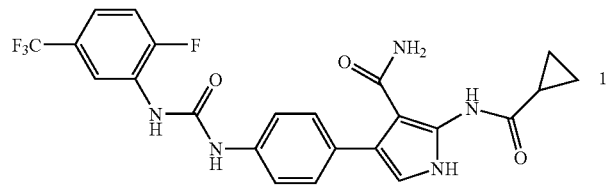

2-(Cyclopropylcarbonylamino)-4-{4-[3-(2-fluoro-5-trifluoromethylphenyl)-ureido]phenyl}-1H-pyrrole-3-carboxamide 2-(Cyclopropylcarbonylamino)-4-{4-[3-(2-fluoro-5-trifluoromethylphenyl)-ureido]phenyl}-1H-pyrrole-3-carboxamide may be prepared as described as described in Example 4 from 2-amino-4-(4-nitrophenyl)-1H-pyrrole-3-carboxamide and cyclopropylcarbonyl chloride. ES+: m/z=490 (MH$^+$).

EXAMPLE 8

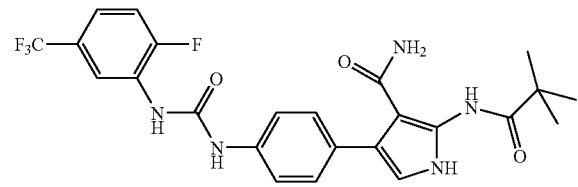

2-Pivaloylamino-4-{4-[3-(2-fluoro-5-trifluoromethylphenyl)ureido]phenyl}-1H-pyrrole-3-carboxamide 2-Pivaloylamino-4-{4-[3-(2-fluoro-5-trifluoromethylphenyl)ureido]phenyl}-1H-pyrrole-3-carboxamide may be prepared as described in Example 4 from 2-amino-4-(4-nitrophenyl)-1H-pyrrole-3-carboxamide and pivaloyl chloride ES+: m/z=506 (MH$^+$).

EXAMPLE 9

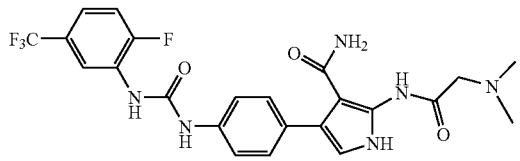

2-(2-Dimethylaminoacetylamino)-4-{4-[3-(2-fluoro-5-trifluoromethylphenyl)-ureido]phenyl}-1H-pyrrole-3-carboxamide 2-(2-Dimethylaminoacetylamino)-4-{4-[3-(2-fluoro-5-trifluoromethylphenyl)-ureido]phenyl}-1H-pyrrole-3-carboxamide may be prepared as described in Example 4 from 2-amino-4-(4-nitrophenyl)-1H-pyrrole-3-carboxamide and dimethylglycine acid chloride ES+: m/z=507 (MH$^+$).

EXAMPLE 10

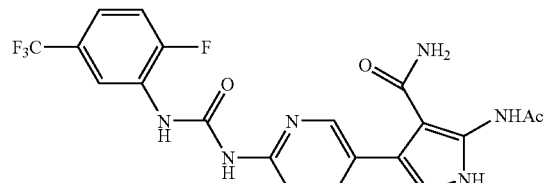

2-Acetylamino-4-{6-[3-(2-fluoro-5-trifluoromethylphenyl)ureido]pyridin-3-yl}-1H-pyrrole-3-carboxamide 0.068 cm$^3$ (0.466 mmol) of 2-fluoro-5-trifluoromethylphenyl isocyanate is added at a temperature in the region of 23° C. and under an argon atmosphere to 0.11 g (0.424 mmol) of 2-acetylamino-4-(6-aminopyridin-3-yl)-1H-pyrrole-3-carboxamide in solution in 20 cm$^3$ of tetrahydrofuran. After stirring for 1 hour at a temperature in the region of 20° C., 0.059 cm$^3$ (0.424 mmol) of triethylamine is added to the medium. The reaction mixture is then stirred for 18 hours at this temperature and then concentrated to dryness under reduced pressure (2.7 kPa). The residue is purified by flash chromatography [eluent: dichloromethane/methanol (95/5 by volume) and pure ethyl acetate gradient]. After concentrating the fractions under reduced pressure, 0.013 g of 2-acetylamino-4-{6-[3-(2-fluoro-5-trifluoromethylphenyl)ureido]pyridin-3-yl}-1H-pyrrole-3-carboxamide is obtained in the form of a white solid. ES$^+$: m/z=466 (MH$^+$).

2-Acetylamino-4-(6-aminopyridin-3-yl)-1H-pyrrole-3-carboxamide may be prepared in the following manner:

0.15 g (0.519 mmol) of 2-acetylamino-4-(6-nitropyridin-3-yl)-1H-pyrrole-3-carboxamide is added at a temperature in the region of 25° C. to a suspension of 0.015 g (0.014 mmol) of 10% palladium on carbon in 20 cm$^3$ of methanol. After hydrogenating for 2 hours in an autoclave under 2 bar of hydrogen, at a temperature in the region of 30° C., the reaction mixture is filtered, the catalyst is rinsed with twice 2 cm$^3$ of ethyl ether. After draining and drying, 0.11 g of 2-acetylamino-4-(6-aminopyridin-3-yl)-1H-pyrrole-3-carboxamide is obtained, in the form of a brown solid. $^1$H NMR (400 MHz, (CD$_3$)$_2$SO, —δ in ppm) 2.13 (s, 3H); 6.01 (broad s, 2H); from 5.50 to 8.85 (very broad m, 2H); 6.35 (d, J=2.5 Hz, 1H); 6.49 (d, J=8.5 Hz, 1H); 7.36 (dd, J=2.5 and 8.5 Hz, 1H); 7.87 (d, J=2.5 Hz, 1H); 10.65 (s, 1H); 11.35 (broad s, 1H).

2-Acetylamino-4-(6-nitropyridin-3-yl)-1H-pyrrole-3-carboxamide may be prepared in the following manner:

0.226 cm$^3$ (1.62 mmol) of triethylamine and 0.058 cm$^3$ (0.809 mmol) of acetyl chloride are added, at a temperature close to 20° C. under an argon atmosphere, to a solution of 0.20 g (0.809 mmol) of 2-amino-4-(6-nitropyridin-3-yl)-1H-pyrrole-3-carboxamide in 40 cm$^3$ of tetrahydrofuran. After stirring for 3 hours at this temperature, the reaction medium is concentrated to dryness under reduced pressure (2.7 kPa) to give a residue which is diluted in 200 cm$^3$ of ethyl acetate and then washed with 50 cm³ of water and 50 cm³ of a saturated aqueous sodium chloride solution, dried over anhydrous magnesium sulphate, filtered and concentrated to dryness under reduced pressure (2.7 kPa) to give 0.15 g of 2-acetylamino-4-(6-nitropyridin-3-yl)-1H-pyrrole-3-carboxamide in the form of a green powder. $^1$H NMR (400 MHz, (CD$_3$)$_2$SO, —δ in ppm) 2.11 (s, 3H); 6.90 (broad m, 2H); 6.95 (d, J=3.0 Hz, 1H); 8.13 (dd, J=2.5 and 8.5 Hz, 1H); 8.27 (d, J=8.5 Hz, 1H); 8.65 (d, J=2.5 Hz, 1H); 10.2 (s, 1H); 11.7 (broad m, 1H).

2-Amino-4-(6-nitro-3-pyridyl)-1H-pyrrole-3-carboxamide may be prepared in the following manner:

4.5 cm³ of concentrated sulphuric acid are added to 0.17 g (0.742 mmol) of 2-amino-4-(6-nitro-3-pyridin-3-yl)-1H-pyrrole-3-carbonitrile at a temperature in the region of 5° C. The mixture is heated at a temperature in the region of 85° C. for 1 hour under an argon atmosphere. After having cooled the reaction mixture to 5° C., it is poured over crushed ice and 30 cm³ of water. This solution is poured over a solution of 300 cm³ of tetrahydrofuran and 15 cm³ of pyridine. After stirring for 5 minutes, the organic phase is washed with 30 cm³ of a saturated aqueous sodium chloride solution and then dried over anhydrous magnesium sulphate, filtered and concentrated to dryness under reduced pressure (2.7 kPa) to give 0.20 g of 2-amino-4-(6-nitropyridin-3-yl)-1H-pyrrole-3-carboxamide in the form of a brown solid. ES+: m/z=248 (MH$^+$).

2-Amino-4-(6-nitropyridin-3-yl)-1H-pyrrole-3-carbonitrile may be prepared in the following manner:

0.022 g (0.336 mmol) of malononitrile is added at a temperature in the region of 20° C., under an argon atmosphere, to 0.050 g (0.224 mmol) of N-[2-(6-nitropyridin-3-yl)-2-oxoethyl]acetamide in solution in 5 cm³ of methanol. The reaction medium is cooled to a temperature in the region of 0° C. and then 0.1 cm³ of a 50% aqueous potassium hydroxide solution is added. After stirring for 15 minutes at a temperature in the region of 20° C. and then for 1.15 hours at a temperature in the region of 65° C., the reaction mixture is concentrated to dryness under reduced pressure (2.7 kPa) and then diluted in 50 cm³ of ethyl acetate. The organic phase is washed with 10 cm³ of water and 10 cm³ of a saturated aqueous sodium chloride solution and then dried over anhydrous magnesium sulphate, filtered and concentrated to dryness under reduced pressure (2.7 kPa) to give 0.043 g of 2-amino-4-(6-nitropyridin-3-yl)-1H-pyrrole-3-carbonitrile in the form of a brown solid. ES+: m/z=230 (MH$^+$).

N-[2-(6-Nitropyridin-3-yl)-2-oxoethyl]acetamide may be prepared in the following manner:

1.575 cm³ (16.66 mmol) of acetic anhydride and then 1.367 g (16.66 mmol) of sodium acetate in solution in 3 cm³ of water are added at a temperature in the region of 5° C. to 1.05 g (4.166 mmol) of 2-amino-1-(6-nitropyridin-3-yl)-ethanone in solution in 25 cm³ of water. After stirring for 3 hours at 5° C., the reaction mixture is extracted with three times 10 cm³ of ethyl acetate. All the organic phases are combined, washed with 30 cm³ of a saturated aqueous sodium chloride solution and then dried over anhydrous magnesium sulphate, filtered and concentrated to dryness under reduced pressure (2.7 kPa) to give 0.618 g of N-[2-(6-nitropyridin-3-yl)-2-oxoethyl]acetamide, in the form of a yellow solid. $^1$H NMR (400 MHz, (CD$_3$)$_2$SO, —δ in ppm) 1.90 (s, 3H); 4.66 (d, J=4.5 Hz, 2H); 8.37 (broad t, J=4.5 Hz, 1H); 8.43 (d, J=8.5 Hz, 1H); 8.68 (dd, J=2.0 and 8.5 Hz, 1H); 9.16 (d, J=2.0 Hz, 1H). 2-Amino-1-(6-nitropyridin-3-yl)ethanone may be prepared in the following manner:

A solution of 1.549 g (6.322 mmol) of 2-bromo-1-(6-nitropyridin-3-yl)ethanone in 25 cm³ of chlorobenzene is added at a temperature in the region of 20° C. to a solution of 0.975 g (6.954 mmol) of hexamethylenetetraamine in 10 cm³ of chlorobenzene. After stirring for 1 hour at this temperature, the suspension is heated for 18 hours at 50° C. The reaction medium is then cooled to 5° C. and then diluted with 200 cm³ of ethyl ether. The precipitate thus obtained is filtered and washed with three times 50 cm³ of ethyl ether. The resulting ammonium salt is stirred in 20 cm³ of ethanol and then 8 cm³ of 37% hydrochloric acid are added at a temperature in the region of 20° C. The solution is then stirred for 16 hours at this temperature. The precipitate formed is filtered, washed with three times 50 cm³ of water, drained and dried to give 1.05 g of 2-amino-1-(6-nitropyridin-3-yl)ethanone in the form of a cream powder. ES+: m/z=182 (MH$^+$).

2-Bromo-1-(6-nitropyridin-3-yl)ethanone may be prepared in the following manner:

7.28 g (40.92 mmol) of N-bromosuccinimide are added to a solution of 3.4 g (20.46 mmol) of 1-(6-nitropyridin-3-yl)ethanone in 60 cm³ of tetrahydrofuran, at a temperature in the region of 20° C. After heating under reflux for 36 hours, the reaction mixture is concentrated to dryness under reduced pressure (2.7 kPa) and then purified by flash chromatography [eluent: pure dichloromethane]. After concentrating the fractions under reduced pressure, 1.7 g of 2-bromo-1-(6-nitropyridin-3-yl)ethanone are obtained in the form of a white powder. ES+: m/z=246 (MH$^+$).

1-(6-Nitropyridin-3-yl)ethanone may be prepared in the following manner:

1.14 g (1.99 mmol) of bis(dibenzylideneacetone)palladium and 10.1 g (49.75 mmol) of 5-bromo-2-nitropyridine are added at a temperature in the region of 20° C. under an argon atmosphere to a solution of 1.044 g (3.98 mmol) of triphenylphosphine in 10 cm³ of toluene. After stirring for 15 minutes at this temperature, a solution of 16.9 cm³ (49.75 mmol) of 1-ethoxy-vinyltributyltin in 60 cm³ of toluene is added. After heating under reflux for 15 hours, the reaction medium is cooled to 20° C. and then poured into 500 cm³ of a 1N hydrochloric acid solution and stirred for 16 hours at this temperature. The medium is then extracted with three times 150 cm³ of ethyl acetate. The organic phases are combined and then washed with 300 cm³ of water, dried over anhydrous magnesium sulphate, filtered and concentrated to dryness under reduced pressure (2.7 kPa) to give a residue which is purified by flash chromatography [eluent: pure dichloromethane]. After concentrating the fractions under reduced pressure, 3.4 g of 1-(6-nitropyridin-3-yl)ethanone are obtained. $^1$H NMR (400 MHz, (CD$_3$)$_2$SO, —δ in ppm) 2.71 (s, 3H); 8.42 (d, J=8.5 Hz, 1H); 8.66 (dd, J=2.5 and 8.5 Hz, 1H); 9.15 (d, J =2.5 Hz, 1H).

EXAMPLE 11

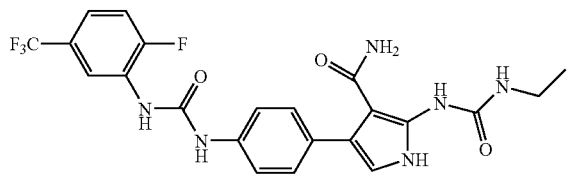

2-(3-Ethylureido)-4-{4-[3-(2-fluoro-5-trifluoromethylphenyl)ureido]phenyl}-1H-pyrrole-3-carboxamide 0.031 cm³ (0.0213 mmol) of 2-fluoro-5-trifluoromethylphenyl isocyanate is added at a temperature in the region of 25° C. to 0.056 g (0.194 mmol) of 4-(4-aminophenyl)-2-(3-ethylureido)-1H-pyrrole-3-carboxamide in solution in 20 cm³ of tetrahydrofuran. After stirring for 16 hours at a temperature in the region of 60° C., the reaction mixture is concentrated to dryness under reduced pressure (2.7 kPa). The residue is then diluted in 40 cm³ of ethyl acetate and then washed with twice 30 cm³ of water. The organic solution is dried over anhydrous magnesium sulphate, filtered and concentrated to dryness under reduced pressure (2.7 kPa) to give a residue which is purified by flash chromatography [eluent: dichloromethane/methanol/acetonitrile (95/2.5/2.5 by volume)]. After concentrating the fractions under reduced pressure, 0.021 g of 2-(3-ethylureido)-4-{4-[3-(2-fluoro-5-trifluoromethylphenyl)ureido]phenyl}-1H-pyrrole-3-carboxamide is obtained in the form of a yellow solid. ES+: m/z=494 (MH⁺).

4-(4-Aminophenyl)-2-(3-ethylureido)-1H-pyrrole-3-carboxamide may be prepared in the following manner:

0.115 g (0.362 mmol) of 4-(4-nitrophenyl)-2-(3-ethylureido)-1H-pyrrole-3-carboxamide is added at a temperature in the region of 25° C. to a suspension of 0.067 g (0.0636 mmol) of 10% palladium on carbon in 15 cm³ of methanol. After hydrogenating for 2.5 hours in an autoclave under 2 bar of hydrogen, at a temperature in the region of 25° C., the reaction mixture is filtered, the catalyst is rinsed with three times 5 cm³ of methanol and then the filtrate is concentrated to dryness under reduced pressure (2.7 kPa) to give 0.056 g of 4-(4-aminophenyl)-2-(3-ethylureido)-1H-pyrrole-3-carboxamide, in the form of an orange solid; ES+: m/z=289 (MH⁺).

4-(4-Nitrophenyl)-2-(3-ethylureido)-1H-pyrrole-3-carboxamide may be prepared in the following manner:

0.074 cm³ (0.891 mmol) of ethyl isocyanate and 0.005 mg (0.040 mmol) of dimethylaminopyridine are added, at a temperature close to 25° C., to a solution of 0.2 g (0.81 mmol) of 2-amino-4-(4-nitrophenyl)-1H-pyrrole-3-carboxamide in 15 cm³ of tetrahydrofuran. After stirring for 16 hours at a temperature close to 60° C., the reaction medium is concentrated to dryness under reduced pressure (2.7 kPa) to give a residue which is stirred in 100 cm³ of water and then extracted with three times 50 cm³ of ethyl acetate. The organic phase is dried over anhydrous magnesium sulphate, filtered and concentrated to dryness under reduced pressure (2.7 kPa) to give a residue which is purified by flash chromatography [eluent: dichloromethane/methanol/acetonitrile (95/2.5/2.5 by volume)]. After concentrating the fractions under reduced pressure, 0.120 g of 4-(4-nitrophenyl)-2-(3-ethylureido)-1H-pyrrole-3-carboxamide is obtained in the form of a yellow powder. ES+: m/z=318 (MH⁺).

2-Amino-4-(4-nitrophenyl)-1H-pyrrole-3-carboxamide is prepared as described in Example 2.

EXAMPLE 12

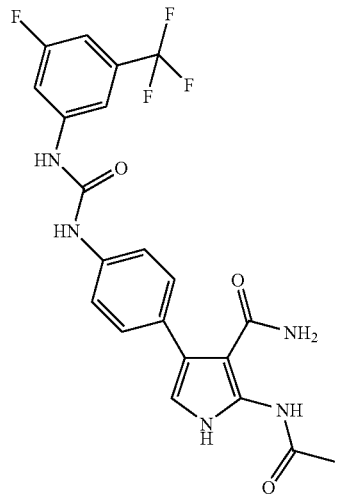

2-Acetylamino-4-{4-[3-(3-fluoro-5-trifluoromethylphenyl)ureido]phenyl}-1H-pyrrole-3-carboxamide 0.061 cm³ (0.426 mmol) of 3-fluoro-5-trifluoromethylphenyl isocyanate is added at room temperature to a suspension of 100 mg (0.387 mmol) of 2-acetylamino-4-(4-aminophenyl)-1H-pyrrole-3-carboxamide in 5 cm³ of anhydrous tetrahydrofuran. The reaction medium is stirred at room temperature for 24 hours, cooled in a water-ice bath and then filtered on sintered glass. The solid collected is washed with a small amount of dichloromethane and cyclohexane and then dried under vacuum. 75 mg of 2-acetylamino-4-{4-[3-(3-fluoro-5-trifluoromethylphenyl)ureido]phenyl}-1H-pyrrole-3-carboxamide are obtained in the form of a beige solid.

LCMS (method A): m/z=464; [M+H]⁺; m/z=447: [M+H]⁺—NH₃ (base peak) m/z=462: [M−H]⁻

Retention time (min.)=3.97

2-Acetylamino-4-(4-aminophenyl)-1H-pyrrole-3-carboxamide may be prepared in the following manner:

0.15 g of palladium on carbon (10%) is added to a suspension of 1.36 g (4.72 mmol) of 2-acetylamino-4-(4-nitrophenyl)-1H-pyrrole-3-carboxamide in 200 cm³ of methanol. The reaction is hydrogenated under 2 bar at 30° C. for 6 hours and then the reaction medium is filtered on celite, washed with methanol. The filtrate is evaporated under reduced pressure and 1.14 g of 2-acetylamino-4-(4-aminophenyl)-1H-pyrrole-3-carboxamide in the form of a brown solid are obtained.

¹H NMR (300 MHz, (CD₃)₂SO d6—δ in ppm): 2.13 (s, 3H); 5.13 (s, 2H); 5.45 (broad m, 1H); 6.24 (d, J=2.5 Hz, 1H); 6.59 (d, J=8.5 Hz, 2H); from 6.90 to 7.10 (broad m, 1H); 6.99 (d, J=8.5 Hz, 2H); 10.8 (s, 1H); 11.25 (broad s, 1H).

EI: m/z=258: [M⁺] (base peak); m/z=241: [M+H]⁺—NH₃; m/z=199: 241-COCH₃

2-Acetylamino-4-(4-nitrophenyl)-1H-pyrrole-3-carboxamide may be prepared in the following manner:

0.851 cm³ (11.960 mmol) of acetyl chloride is added at room temperature to a suspension of 2.16 g (8.77 mmol) of 2-amino-4-(4-nitrophenyl)-1H-pyrrole-3-carboxamide in 200 cm³ of dried tetrahydrofuran under argon. The mixture is cooled in a water-ice bath and then 3.180 cm³ (22.82 mmol) of triethylamine are slowly added at 0° C. The reaction is stirred at 0° C. for 15 minutes and then at room temperature for 3 hours. The medium is taken up in ethyl acetate and then the organic phase is washed with water and then dried over magnesium sulphate, filtered and the solvents are evaporated under reduced pressure. The crude product is purified by flash chromatography [eluent: dichloromethane/methanol (99/1 by volume)]. After concentrating under reduced pressure the fractions containing the expected product, 1.23 g of 2-acetylamino-4-(4-nitrophenyl)-1H-pyrrole-3-carboxamide are obtained in the form of a brown solid.

$^1$H NMR (400 MHz, $(CD_3)_2SO$ d6—δ in ppm): 2.11 (s, 3H); from 6.50 to 7.20 (very broad m, 2H); 6.80 (s, 1H); 7.63 (d, J=9.0 Hz, 2H); 8.18 (d, J=9.0 Hz, 2H); 10.3 (broad s, 1H); 11.6 (broad s, 1H).

LCMS (method A); m/z=287: [M−H]$^-$

Retention time (min)=2.90

2-Amino-4-(4-nitrophenyl)-1H-pyrrole-3-carboxamide may be prepared as described in Example 2 from 2-amino-4-(4-nitrophenyl)-1H-pyrrole-3-carbonitrile.

EXAMPLE 13

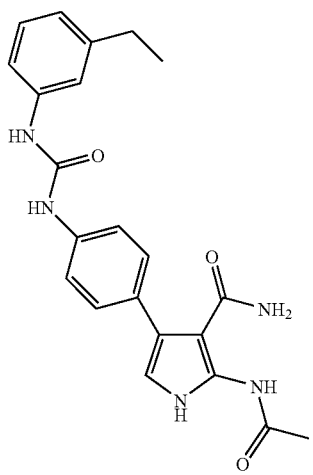

2-Acetylamino-4-{4-[3-(3-ethylphenyl)ureido]phenyl}-1H-pyrrole-3-carboxamide 0.061 cm$^3$ (0.426 mmol) of 1-ethyl-3-isocyanatobenzene is added at room temperature to a suspension of 100 mg (0.387 mmol) of 2-acetylamino-4-(4-aminophenyl)-1H-pyrrole-3-carboxamide in 5 cm$^3$ of anhydrous tetrahydrofuran. The reaction medium is stirred at room temperature for 24 hours and then evaporated to dryness under reduced pressure. The crude product is purified by flash chromatography [eluent; dichloromethane/methanol (97/3 by volume)]. After concentrating under reduced pressure the fractions containing the expected product, 107 mg of 2-acetylamino-4-{4-[3-(3-ethylphenyl)ureido]phenyl}-1H-pyrrole-3-carboxamide are obtained in the form of a brown solid.

LCMS (method A);

m/z=406: [M+H]$^+$ m/z=389: [M+H]$^+$—NH$_3$

Retention time (min)=3.67

EXAMPLE 14

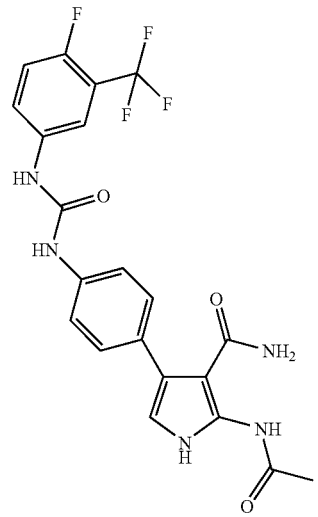

2-Acetylamino-4-{4-[3-(4-fluoro-3-trifluoromethylphenyl)ureido]phenyl}-1H-pyrrole-3-carboxamide 2-Acetylamino-4-{4-[3-(4-fluoro-3-trifluoromethylphenyl)ureido]phenyl}-1H-pyrrole-3-carboxamide may be prepared as described in Example 13 from 4-fluoro-3-(trifluoromethyl)phenyl isocyanate and 2-acetylamino-4-(4-aminophenyl)-1H-pyrrole-3-carboxamide. Its characteristics are the following:

LCMS (method A):

m/z=464: [M+H]$^+$; m/z 447: [M+H]$^+$—NH$_3$ (base peak)

m/z=462: [M−H]$^-$

Retention time (min)=3.83

EXAMPLE 15

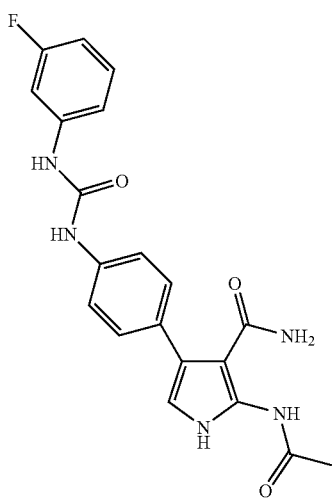

2-Acetylamino-4-{4-[3-(3-fluorophenyl)ureido]phenyl}-1H-pyrrole-3-carboxamide

2-Acetylamino-4-{4-[3-(3-fluorophenyl)ureido]phenyl}-1H-pyrrole-3-carboxamide may be prepared as described in Example 12 from 3-fluoro-phenyl isocyanate and 2-acetylamino-4-(4-aminophenyl)-1H-pyrrole-3-carboxamide. Its characteristics are the following:

LCMS (method A): m/z=396: [M+H]$^+$; m/z=379: [M+H]$^+$—NH$_3$

Retention time (min)=3.42

EXAMPLE 16

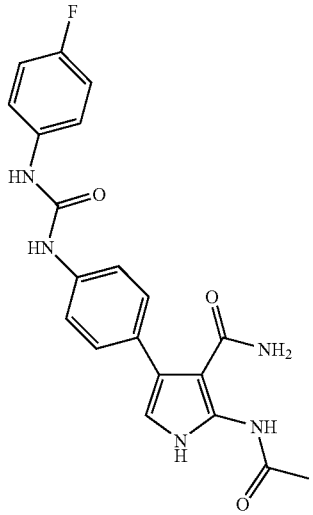

2-Acetylamino-4-{4-[3-(4-fluorophenyl)ureido]phenyl}-1H-pyrrole-3-carboxamide

2-Acetylamino-4-{4-[3-(4-fluorophenyl)ureido]phenyl}-1H-pyrrole-3-carboxamide may be prepared as described in Example 12 from 4-fluoro-phenyl isocyanate and 2-acetylamino-4-(4-aminophenyl)-1H-pyrrole-3-carboxamide.

LCMS (method A): m/z=396: [M+H]$^+$; m/z=379: [M+H]$^+$—NH$_3$

Retention time (min)=3.42

EXAMPLE 17

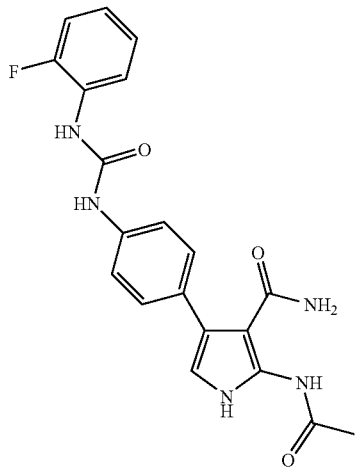

2-Acetylamino-4-{4-[3-(2-fluorophenyl)ureido]phenyl}-1H-pyrrole-3-carboxamide

2-Acetylamino-4-{4-[3-(2-fluorophenyl)ureido]phenyl}-1H-pyrrole-3-carboxamide may be prepared as described in Example 12 from 2-fluorophenyl isocyanate and 2-acetylamino-4-(4-aminophenyl)-1H-pyrrole-3-carboxamide.

LCMS (method B): m/z=396: [M+H]$^+$ (base peak); m/z=379: [M+H]$^+$—NH$_3$

Retention time (min)=3.70

EXAMPLE 18

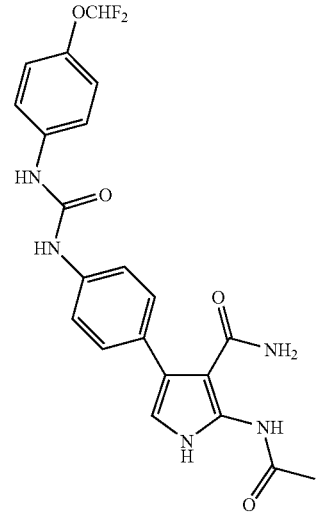

2-Acetylamino-4-{4-[3-(4-difluoromethoxyphenyl)ureido]phenyl}-1H-pyrrole-3-carboxamide 2-Acetylamino-4-{4-[3-(4-difluoromethoxyphenyl)ureido]phenyl}-1H-pyrrole-3-carboxamide may be prepared as described in Example 12 from 4-(difluoromethoxy)phenyl isocyanate and 2-acetylamino-4-(4-aminophenyl)-1H-pyrrole-3-carboxamide.

LCMS (method A):

m/z=444: [M+H]$^+$; m/z 427: [M+H]$^+$—NH$_3$ m/z=442: [M−H]$^-$

Retention time (min)=3.51

EXAMPLE 19

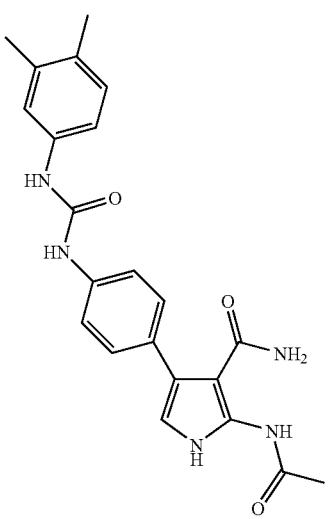

2-Acetylamino-4-{4-[3-(3,4-dimethylphenyl)ureido]phenyl}-1H-pyrrole-3-carboxamide 2-Acetylamino-4-{4-[3-(3,4-dimethylphenyl)ureido]phenyl}-1H-pyrrole-3-carboxamide may be prepared as described in Example 12 from 3,4-dimethyl-phenyl isocyanate and 2-acetylamino-4-(4-aminophenyl)-1H-pyrrole-3-carboxamide.

LCMS (method A):
m/z=406: [M+H]⁺, m/z=389: [M+H]⁺—NH₃
m/z=404: [M−H]⁻
Retention time (min)=3.60

EXAMPLE 20

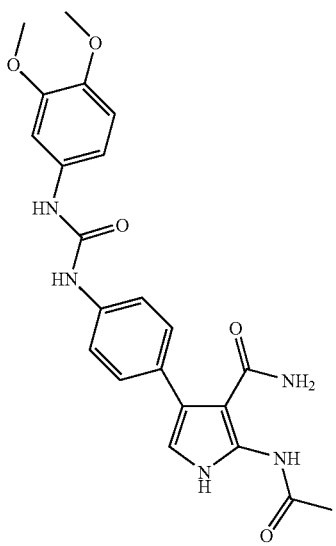

2-Acetylamino-4-{4-[3-(3,4-dimethoxyphenyl)ureido]phenyl}-1H-pyrrole-3-carboxamide 2-Acetylamino-4-{4-[3-(3,4-dimethoxyphenyl)ureido]phenyl}-1H-pyrrole-3-carboxamide may be prepared as described in Example 12 from 3,4-dimethoxyphenyl isocyanate and 2-acetylamino-4-(4-aminophenyl)-1H-pyrrole-3-carboxamide.

LCMS (method A):
m/z=438: [M+H]⁺; m/z=421: [M+H]⁺—NH₃
m/z=436: [M−H]
Retention time (min)=2.94

EXAMPLE 21

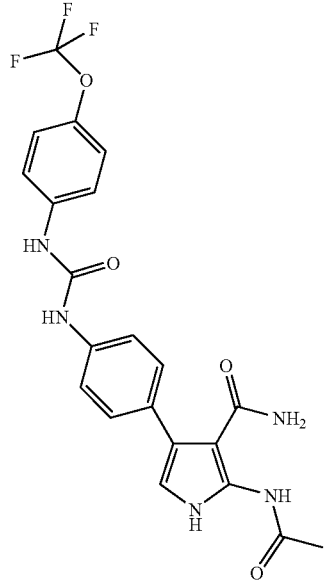

2-Acetylamino-4-{4-[3-(4-trifluoromethoxyphenyl)ureido]phenyl}-1H-pyrrole-3-carboxamide 2-Acetylamino-4-{4-[(3-(4-trifluoromethoxyphenyl)ureido]phenyl}-1H-pyrrole-3-carboxamide may be prepared as described in Example 12 from 4-(trifluoromethoxy)phenyl isocyanate and 2-acetylamino-4-(4-aminophenyl)-1H-pyrrole-3-carboxamide.

LCMS (method A):
m/z=462: [M+H]⁺; m/z=445: [M+H]⁺—NH₃
m/z=460: [M−H]⁻
Retention time (min)=3.85

EXAMPLE 22

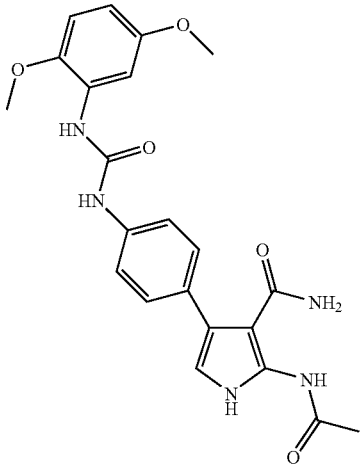

2-Acetylamino-4-{4-[3-(2,5-dimethoxyphenyl)ureido]phenyl}-1H-pyrrole-3-carboxamide 2-Acetylamino-4-{4-[3-(2,5-dimethoxyphenyl)ureido]phenyl}-1H-pyrrole-3-carboxamide may be prepared as described in Example 13 from 2,5-dimethoxyphenyl isocyanate and 2-acetylamino-4-(4-aminophenyl)-1H-pyrrole-3-carboxamide.

LCMS (method C):
m/z=438: [M+H]+
m/z=436: [M−H]−
Retention time (min)=3.16

EXAMPLE 23

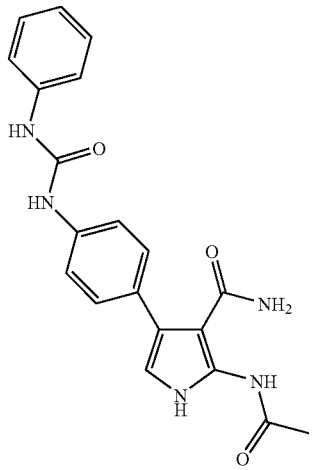

2-Acetylamino-4-[4-(3-phenylureido)phenyl]-1H-pyrrole-3-carboxamide

2-Acetylamino-4-[4-(3-phenylureido)phenyl]-1H-pyrrole-3-carboxamide may be prepared as described in Example 13 from phenyl isocyanate and 2-acetylamino-4-(4-aminophenyl)-1H-pyrrole-3-carboxamide.
LCMS (method C):
m/z=378: [M+H]+
m/z=376: [M−H]−
Retention time (min)=2.97

EXAMPLE 24

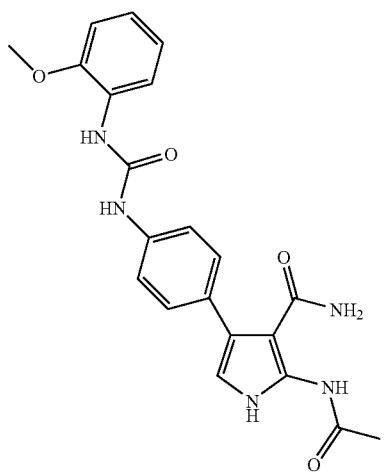

2-Acetylamino-4-{4-[3-(2-methoxyphenyl)ureido]phenyl}-1H-pyrrole-3-carboxamide

2-Acetylamino-4-{4-[3-(2-methoxyphenyl)ureido]phenyl}-1H-pyrrole-3-carboxamide may be prepared as described in Example 13 from 2-methoxyphenyl isocyanate and 2-acetylamino-4-(4-aminophenyl)-1H-pyrrole-3-carboxamide.

LCMS (method C):
m/z=408: [M+H]+
m/z=406: [M−H]−
Retention time (min)=3.16

EXAMPLE 25

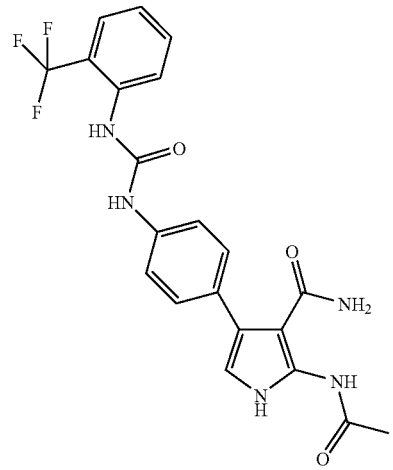

2-Acetylamino-4-{4-[3-(2-trifluoromethylphenyl)ureido]phenyl}-1H-pyrrole-3-carboxamide 2-Acetylamino-4-{4-[3-(2-trifluoromethylphenyl)ureido]phenyl}-1H-pyrrole-3-carboxamide may be prepared as described in Example 13 from 2-(trifluoromethyl)phenyl isocyanate and 2-acetylamino-4-(4-aminophenyl)-1H-pyrrole-3-carboxamide.
LCMS (method C):
m/z=446: [M+H]+
m/z=444: [M−H]−
Retention time (min)=3.32

EXAMPLE 26

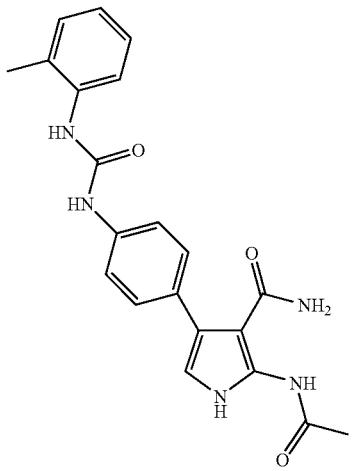

2-Acetylamino-4-[4-(3-o-tolylureido)phenyl]-1H-pyrrole-3-carboxamide

2-Acetylamino-4-[4-(3-o-tolylureido)phenyl]-1H-pyrrole-3-carboxamide may be prepared as described in Example 13 from 2-methylphenyl isocyanate and 2-acetylamino-4-(4-aminophenyl)-1H-pyrrole-3-carboxamide.

LCMS (method C):
m/z=392: [M+H]+
m/z=390: [M−H]−
Retention time (min)=3.07

EXAMPLE 27

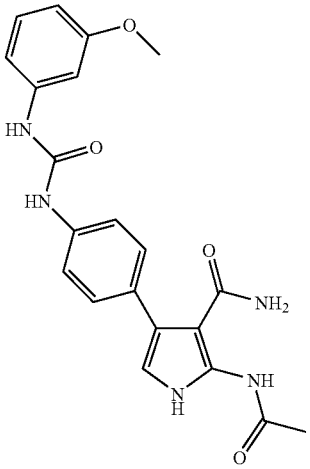

2-Acetylamino-4-{4-[3-(3-methoxyphenyl)ureido]phenyl}-1H-pyrrole-3-carboxamide

2-Acetylamino-4-{4-[3-(3-methoxyphenyl)ureido]phenyl}-1H-pyrrole-3-carboxamide may be prepared as described in Example 13 from 3-methoxyphenyl isocyanate and 2-acetylamino-4-(4-aminophenyl)-1H-pyrrole-3-carboxamide.

LCMS (method C):
m/z=408: [M+H]+
m/z=406: [M−H]−
Retention time (min)=3.01

EXAMPLE 28

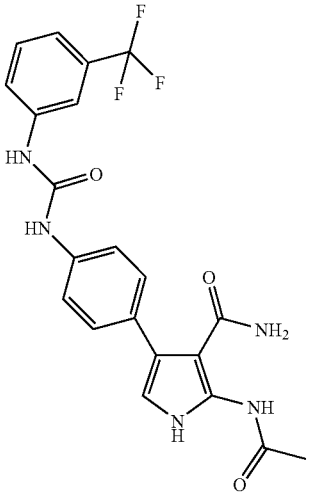

2-Acetylamino-4-{4-[3-(3-trifluoromethylphenyl)ureido]phenyl}-1H-pyrrole-3-carboxamide 2-Acetylamino-4-{4-[3-(3-trifluoromethylphenyl)ureido]phenyl}-1H-pyrrole-3-carboxamide may be prepared as described in Example 13 from 3-(trifluoromethyl)phenyl isocyanate and 2-acetylamino-4-(4-aminophenyl)-1H-pyrrole-3-carboxamide.

LCMS (method C):
m/z=446: [M+H]+
m/z=444: [M−H]−
Retention time (min)=3.54

EXAMPLE 29

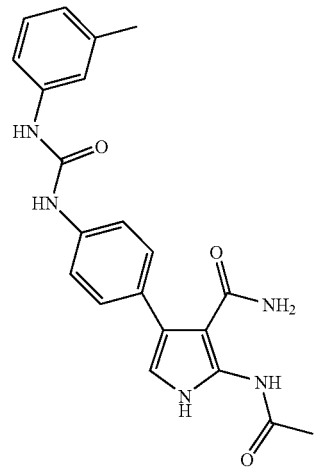

2-Acetylamino-4-[4-(3-m-tolylureido)phenyl]-1H-pyrrole-3-carboxamide

2-Acetylamino-4-[4-(3-m-tolylureido)phenyl]-1H-pyrrole-3-carboxamide may be prepared as described in Example 13 from 3-methylphenyl isocyanate and 2-acetylamino-4-(4-aminophenyl)-1H-pyrrole-3-carboxamide.

LCMS (method C):
m/z=392: [M+H]+
m/z=390: [M−H]−
Retention time (min)=3.20

EXAMPLE 30

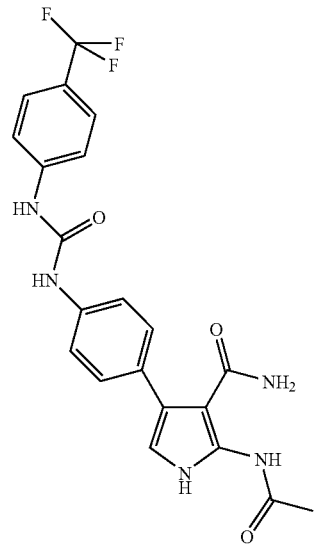

2-Acetylamino-4-{4-[3-(4-trifluoromethylphenyl)ureido]phenyl}-1H-pyrrole-3-carboxamide 2-Acetylamino-4-{4-[3-(4-trifluoromethylphenyl)ureido]phenyl}-1H-pyrrole-3-carboxamide may be prepared as described in Example 13 from 4-(trifluoromethyl)phenyl isocyanate and 2-acetylamino-4-(4-aminophenyl)-1H-pyrrole-3-carboxamide.
LCMS (method C):
m/z=446: [M+H]+
m/z=444: [M–H]−
Retention time (min)=3.58

EXAMPLE 31

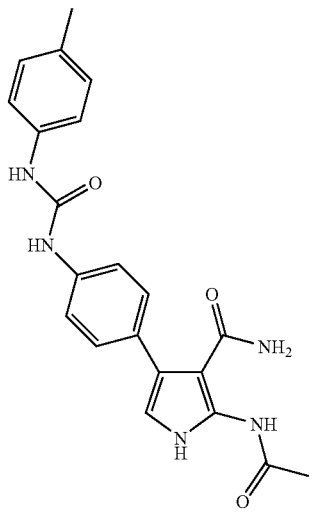

2-Acetylamino-4-[4-(3-p-tolylureido)phenyl]-1H-pyrrole-3-carboxamide

2-Acetylamino-4-[4-(3-p-tolylureido)phenyl]-1H-pyrrole-3-carboxamide may be prepared as described in Example 13 from 4-methylphenyl isocyanate and 2-acetylamino-4-(4-aminophenyl)-1H-pyrrole-3-carboxamide.
LCMS (method C):
m/z=392: [M+H]+
m/z=390: [M–H]−
Retention time (min)=3.19

EXAMPLE 32

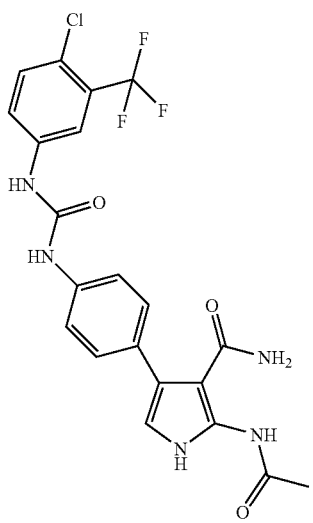

2-Acetylamino-4-{4-[3-(4-chloro-3-trifluoromethylphenyl)ureido]phenyl}-1H-pyrrole-3-carboxamide 2-Acetylamino-4-{4-[3-(4-chloro-3-trifluoromethylphenyl)ureido]-phenyl}-1H-pyrrole-3-carboxamide may be prepared as described in Example 13 from 4-chloro-3-(trifluoromethyl)phenyl isocyanate and 2-acetylamino-4-(4-aminophenyl)-1H-pyrrole-3-carboxamide.
LCMS (method C):
m/z=480: [M+H]+
m/z 478=[M–H]−
Retention time (min)=3.80

EXAMPLE 33

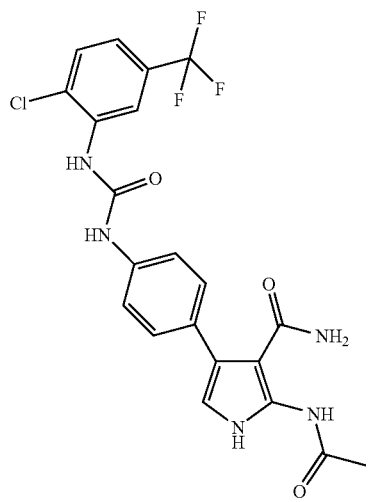

2-Acetylamino-4-{4-[3-(2-chloro-5-trifluoromethylphenyl)ureido]phenyl}-1H-pyrrole-3-carboxamide 2-Acetylamino-4-{4-[3-(2-chloro-5-trifluoromethylphenyl)ureido]phenyl}-1H-pyrrole-3-carboxamide may be prepared as described in Example 13 from 2-chloro-5-(trifluoromethyl)phenyl isocyanate and 2-acetylamino-4-(4-aminophenyl)-1H-pyrrole-3-carboxamide.
LCMS (method C):
m/z=480: [M+H]+
m/z=478: [M–H]−
Retention time (min)=3.82

EXAMPLE 34

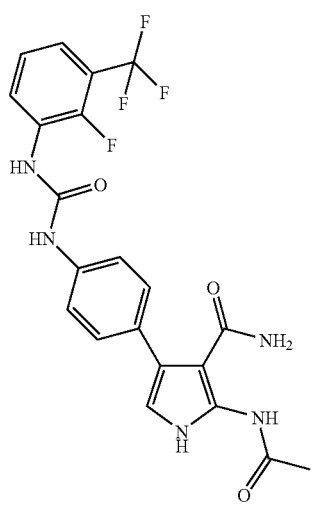

2-Acetylamino-4-{4-[3-(2-fluoro-3-trifluoromethylphenyl)ureido]phenyl}-1H-pyrrole-3-carboxamide 2-Acetylamino-4-{4-[3-(2-fluoro-3-trifluoromethylphenyl)ureido]phenyl}-1H-pyrrole-3-carboxamide may be prepared as described in Example 13 from 2-fluoro-3-(trifluoromethyl)phenyl isocyanate and 2-acetylamino-4-(4-aminophenyl)-1H-pyrrole-3-carboxamide.

LCMS (method C):
m/z=464: [M+H]+
m/z=462: [M−H]−
Retention time (min)=3.64

EXAMPLE 35

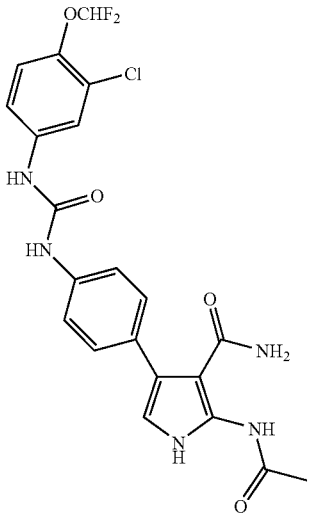

2-Acetylamino-4-{4-[3-(3-chloro-4-difluoromethoxyphenyl)ureido]phenyl}-1H-pyrrole-3-carboxamide 2-Acetylamino-4-{4-[3-(3-chloro-4-difluoromethoxyphenyl)ureido]phenyl}-1H-pyrrole-3-carboxamide may be prepared as described in Example 13 from 3-chloro-4-(difluoromethoxy)phenyl isocyanate and 2-acetylamino-4-(4-aminophenyl)-1H-pyrrole-3-carboxamide.

LCMS (method C):
m/z=478: [M+H]+
m/z=476: [M−H]−
Retention time (min)=3.52

EXAMPLE 36

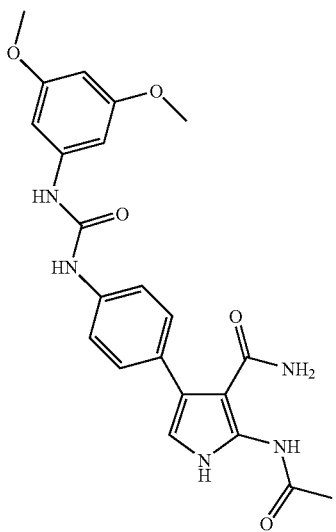

2-Acetylamino-4-{4-[3-(3,5-dimethoxyphenyl)ureido]phenyl}-1H-pyrrole-3-carboxamide 2-Acetylamino-4-{4-[3-(3,5-dimethoxyphenyl)ureido]phenyl}-1H-pyrrole-3-carboxamide may be prepared as described in Example 13 from 3,5-dimethoxyphenyl isocyanate and 2-acetylamino-4-(4-aminophenyl)-1H-pyrrole-3-carboxamide.

LCMS (method C):
m/z=438: [M+H]+
m/z=436: [M−H]−
Retention time (min)=3.07

EXAMPLE 37

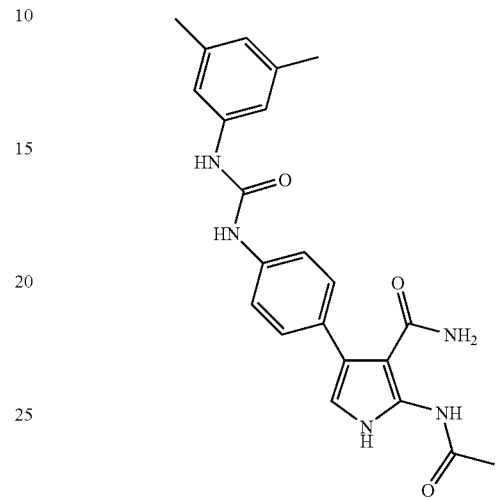

2-Acetylamino-4-{4-[3-(3,5-dimethylphenyl)ureido]phenyl}-1H-pyrrole-3-carboxamide 2-Acetylamino-4-{4-[3-(3,5-dimethylphenyl)ureido]phenyl}-1H-pyrrole-3-carboxamide may be prepared as described in Example 13 from 3,5-dimethylphenyl isocyanate and 2-acetylamino-4-(4-aminophenyl)-1H-pyrrole-3-carboxamide.

LCMS (method C):
m/z=406: [M+H]+
m/z=404: [M−H]−
Retention time (min)=3.43

EXAMPLE 38

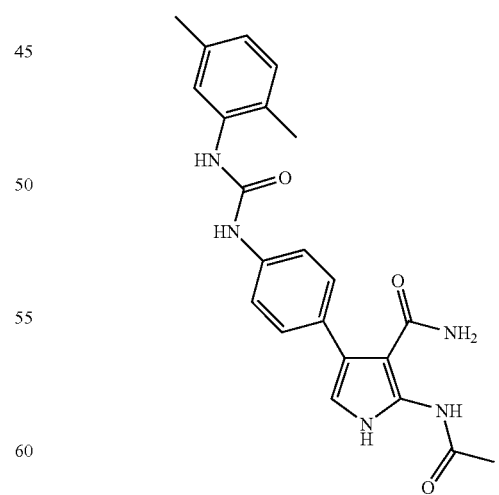

2-Acetylamino-4-{4-[3-(2,5-dimethylphenyl)ureido]phenyl}-1H-pyrrole-3-carboxamide 2-Acetylamino-4-{4-[3-(2,5-dimethylphenyl)ureido]phenyl}-1H-pyrrole-3-carboxamide may be prepared as described in Example 13 from 2,5-dimethylphenyl isocyanate and 2-acetylamino-4-(4-aminophenyl)-1H-pyrrole-3-carboxamide.

LCMS (method C):
m/z=406: [M+H]$^+$
m/z=404: [M−H]$^−$
Retention time (min)=3.29

EXAMPLE 39

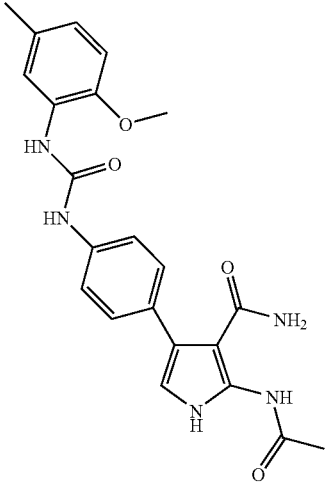

2-Acetylamino-4-{4-[3-(2-methoxy-5-methylphenyl)ureido]phenyl}-1H-pyrrole-3-carboxamide 2-Acetylamino-4-{4-[3-(2-methoxy-5-methylphenyl)ureido]phenyl}-1H-pyrrole-3-carboxamide may be prepared as described in Example 13 from 2-methoxy-5-methylphenyl isocyanate and 2-acetylamino-4-(4-aminophenyl)-1H-pyrrole-3-carboxamide.

LCMS (method C):
m/z=422: [M+H]$^+$
m/z=420: [M−H]$^−$
Retention time (min)=3.38

EXAMPLE 40

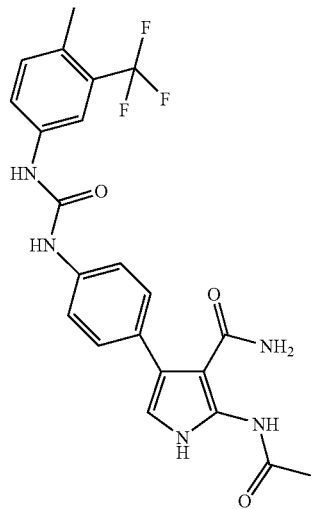

2-Acetylamino-4-{4-[3-(4-methyl-3-trifluoromethylphenyl)ureido]phenyl}-1H-pyrrole-3-carboxamide 2-Acetylamino-4-{4-[3-(4-methyl-3-trifluoromethylphenyl)ureido]phenyl}-1H-pyrrole-3-carboxamide may be prepared as described in Example 13 from 3-(trifluoromethyl)-4-methylphenyl isocyanate and 2-acetylamino-4-(4-aminophenyl)-1H-pyrrole-3-carboxamide.

Melting point=266° C.
ES$^+$: m/z=460: [M+H]$^+$; m/z=482: [M+Na]$^+$

EXAMPLE 41

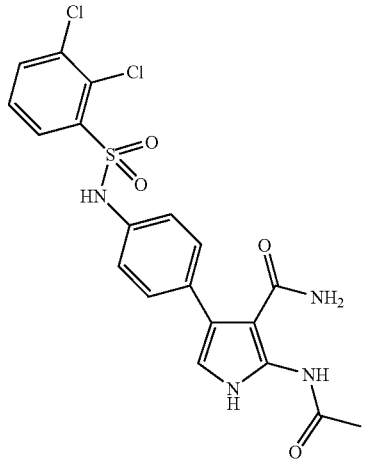

2-Acetylamino-4-[4-(2,3-dichlorobenzenesulphonylamino)phenyl]-1H-pyrrole-3-carboxamide A suspension of 70 mg (0.271 mmol) of 2-acetylamino-4-(4-aminophenyl)-1H-pyrrole-3-carboxamide and 70 mg (0.285 mmol) of 2,3-dichlorobenzene-sulphonyl chloride in 1.5 cm$^3$ of pyridine is stirred at room temperature for 24 hours and then the reaction medium is evaporated to dryness under reduced pressure. The crude product is purified by flash chromatography [eluent; dichloromethane/methanol (97/3 by volume)]. After concentrating under reduced pressure the fractions containing the expected product, 22 mg of 2-acetylamino-4-[4-(2,3-dichlorobenzenesulphonylamino)phenyl]-1H-pyrrole-3-carboxamide are obtained in the form of a beige solid melting at 265° C.

ES$^+$: m/z=469: [M+H]$^+$

Determination of the Activity of the Compounds—Experimental Protocols

1. FAK

The inhibitory activity of the compounds on FAK is determined by a measurement of the inhibition of the autophosphorylation of the enzyme using a time-resolved fluorescence test (HTRF).

The complete human FAK cDNA, whose N-terminal end was labelled with histidine, was cloned into a baculovirus expression vector pFastBac HTc. The protein was expressed and purified at about 70% homogeneity.

The kinase activity is determined by incubating the enzyme (6.6 μg/ml) with various concentrations of test compound in a 50 mM Hepes buffer, pH=7.2, containing 10 mM MgCl$_2$, 100 μM Na$_3$VO$_4$, 15 μM ATP for 1 hour at 37° C. The enzymatic reaction is stopped by adding Hepes buffer, pH=7.0, containing 0.4 mM KF, 133 mM EDTA, 0.1% BSA and the labelling is carried out, for 1 to 2 hours at room temperature, by adding to this buffer an anti-histidine antibody labelled with XL665 and a monoclonal antibody phospho-specific for tyrosine, conjugated with europium cryptate (Eu-K). The characteristics of the two fluorophores are available in G. Mathis et al., Anticancer Research, 1997, 17, pages 3011-3014. The energy transfer between the excited europium cryptate to the acceptor XL665 is proportional to the degree of autophosphorylation of FAK. The signal of long duration specific for XL-665 is measured in a Packard Discovery plate counter. All the assays are performed in duplicate and the mean of the two assays is calculated. The inhibition of the FAK autophosphorylation activity with compounds of the invention is expressed as a percentage inhibition relative to a control whose activity is measured in the absence of test compound. For the calculation of the % inhibition, the [signal at 665 nm/signal at 620 nm] ratio is considered.

2. KDR

The inhibitory effect of the compounds is determined in a test of phosphorylation of substrate by the KDR enzyme in vitro by a scintillation technique (96-well plate, NEN).

The cytoplasmic domain of the human KDR enzyme was cloned in a GST fusion form into the baculovirus expression vector pFastBac. The protein was expressed in SF21 cells and purified to about 60% homogeneity.

The kinase activity of KDR is measured in 20 mM MOPS, 10 mM MgCl2, 10 mM MnCl2, 1 mM DTT, 2.5 mM EGTA, 10 mM b-glycerophosphate, pH=7.2, in the presence of 10 mM MgCl2, 100 µM $Na_3VO_4$, 1 mM NaF. 10 µl of the compound are added to 70 µl of kinase buffer containing 100 ng of KDR enzyme at 4° C. The reaction is initiated by adding 20 µl of solution containing 2 µg of substrate (SH2—SH3 fragment of PLCγ expressed in the form of a GST fusion protein), 2 µCi γ $^{33}$P[ATP] and 2 µM cold ATP. After incubating for 1 hour at 37° C., the reaction is stopped by adding 1 volume (100 µl) of 200 mM EDTA. The incubation buffer is removed and the wells are washed three times with 300 µl of PBS. The radioactivity is measured in each well using a Top Count NXT (Packard) radioactivity counter.

The background noise is determined by measuring the radioactivity in four different wells containing radioactive ATP and the substrate alone.

A control for total activity is measured in four different wells all containing the reagents ($\gamma^{33}$P-[ATP], KDR and PLCγ substrate) but in the absence of compound.

The inhibition of the KDR activity with the compound of the invention is expressed as percentage inhibition of the control activity determined in the absence of compound.

The compound SU5614 (Calbiochem) (1 µM) is included in each plate as control for inhibition.

3. Tie2

The coding sequence for human Tie2 corresponding to the amino acids of the intracellular domain 776-1124 was generated by PCR using the cDNA isolated from human placenta as model. This sequence was introduced into a baculovirus expression vector pFastBacGT in the form of a GST fusion protein.

The inhibitory effect of the molecules is determined in a test of phosphorylation of PLC by Tie2 in the presence of GST-Tie2 purified to about 80% homogeneity. The substrate is composed of the SH2—SH3 fragments of PLC expressed in the form of the GST fusion protein.

The kinase activity of Tie2 is measured in a 20 mM MOPS buffer, pH 7.2, containing 10 mM $MgCl_2$, 10 mM $MnCl_2$, 1 mM DTT, 10 mM glycero-phosphate. A reaction mixture composed of 70 µl of kinase buffer containing 100 ng of GST-Tie2 enzyme per well is deposited in a FlashPlate 96-well plate kept on ice. 10 µl of the test molecule diluted in DMSO to a concentration of 10% maximum are then added. For a given concentration, each measurement is carried out in quadruplicate. The reaction is initiated by adding 20 µl of solution containing 2 µg of GST-PLC, 2 µM of cold ATP and 1 µCi d'$^{33}$P[ATP]. After incubating for 1 hour at 37° C., the reaction is stopped by adding 1 volume (100 µl) of EDTA at 200 mM. After removing the incubation buffer, the wells are washed three times with 300 µl of PBS. The radioactivity is measured on a Wallac MicroBeta1450.

The inhibition of the Tie2 activity is calculated and expressed as a percentage inhibition relative to the control activity determined in the absence of compound.

TABLE 1

Results:

| Structure | Example | FAK IC 50 (nM) | KDR IC 50 (nM) | TEI2 IC 50 (nM) |
|---|---|---|---|---|
| 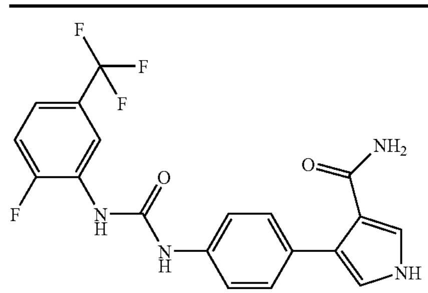 | 1 | 2055 | 6475 | 69 |
| 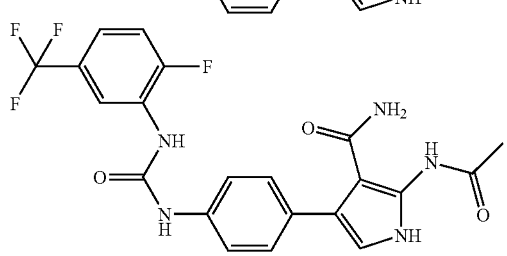 | 2 | 60 | 11.4 | 6.3 |

TABLE 1-continued
Results:
| Structure | Example | FAK IC 50 (nM) | KDR IC 50 (nM) | TIE2 IC 50 (nM) |
|---|---|---|---|---|
| 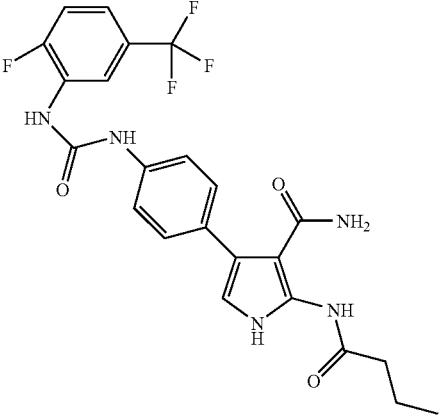 | 5 | 266 | 42 | 11 |
| 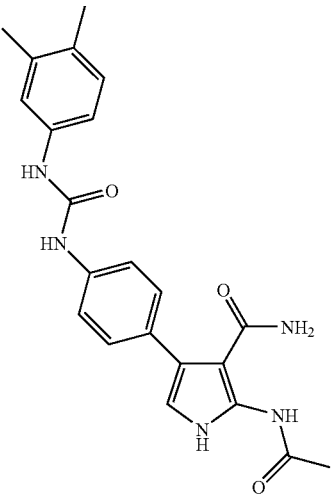 | 19 | 717 | 13 | 125 |
| 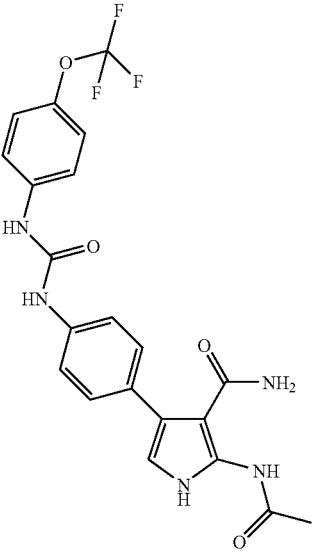 | 21 | 163 | 19 | 118 |

What is claimed is:

1. A compound of formula (I):

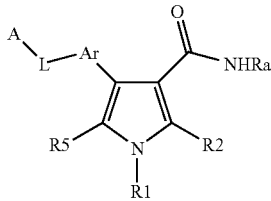

Formula (I)

in which:
1) A and Ar are independently selected from the group consisting of: aryl, heteroaryl, heterocyclyl, substituted aryl, substituted heteroaryl, substituted heterocyclyl, cycloalkyl, and substituted cycloalkyl;
2) L is selected from the group consisting of: NH, CO—NH, NH—CO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$, and NH—CO—CH$_2$—CO—NH;
3) Ra is selected from the group consisting of H, alkyl and cycloalkyl;
4) R1) is selected from the group consisting of: H, R, COR, and SO$_2$R, in which R is chosen from H, OR"$_4$, NR"$_5$R"$_6$, (C1-C6)alkyl, cycloalkyl, heterocyclyl, substituted heterocyclyl, aryl, substituted aryl, heteroaryl, and substituted heteroaryl, in which R"4 is chosen from H, phenyl, and alkyl, and in which R"5 and R"6 are independently selected from the group consisting of H, R OR"$_4$, (C1-C6)alkyl, cycloalkyl, heterocyclyl, substituted heterocyclyl, aryl, substituted aryl, heteroaryl, and substituted heteroaryl or alternatively R"5 and R"6 are linked to each other to form a 5- to 8-membered saturated ring containing from 0 to 3 heteroatoms chosen from O, S and N;
5) R2 and R5 are independently selected from the group consisting of: H, halogen, R'2, CN, O(R'2), OC(O)(R'2), OC(O)N(R'2)(R'3), OS(O$_2$)(R'2), N(R'2)(R'3), N═C(R'2)(R'3), N(R'2)C(O)(R'3), N(R'2)C(O)O(R'3), N(R'4)C(O)N(R'2)(R'3), N(R'4)C(S)N(R'2)(R'3), N(R'2)S(O$_2$)(R'3), C(O)(R'2), C(O)O(R'2), C(O)N(R'2)(R'3), C(═N(R'3))(R'2), C(═N(OR'3))(R'2), S(R'2), S(O)(R'2), S(O$_2$)(R'2), S(O$_2$)O(R'2), and S(O$_2$)N(R'2)(R'3); in which each R'2, R'3, R'4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, and substituted heterocyclyl; in which, when R'2 and R'3 are each different from H and simultaneously present on R2 or on R3, they may be linked to each other to form a ring containing from 0 to 3 heteroatoms chosen from O, S and N;
or a pharmaceutically acceptable salt thereof.

2. A compound according to claim 1, wherein:
R1 is H; L is selected from the group consisting of: NHCO, NH—CO—NH, NH, NHSO$_2$, and NHCO—CH$_2$—CONH; and Ra is selected from H and methyl.

3. A compound according to claim 1, wherein Ar-L-A is:

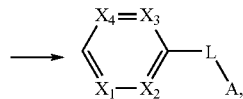

in which each X1, X2, X3 and X4 is independently chosen from N and C—R'5, in which R'5 has the same definition as R2 as defined in claim 1.

4. A compound according to claim 3, wherein R'5 is selected from the group consisting of H, F, Cl, methyl, NH$_2$, OMe, OCF$_3$, and CONH$_2$.

5. A compound according to claim 1, wherein R2 and R5 are independently selected from the group consisting of: H, halogen, R'2, OR'2, NHR'2, NHCOR'3, NHCONHR'2, and NHSO$_2$R'3.

6. A compound according to claim 5, wherein R2 is H.

7. A compound according to claim 5, wherein R5 is H.

8. A compound according to claim 1, wherein Ra is H.

9. A compound according to claim 1, wherein L-A is chosen from NH—CO—NH-A and NH—SO$_2$-A.

10. A compound according to claim 1, wherein A is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl, and benzothiazolyl; each being optionally substituted.

11. A compound according to claim 10, wherein A is chosen from phenyl, pyrazolyl and isoxazolyl; each being optionally substituted.

12. A compound according to claim 10, wherein A is substituted with a first substituent selected from the group consisting of alkyl, halogenated alkyl, alkylene, alkynyl, aryl, heteroaryl, O-alkyl, O-aryl, O-heteroaryl, S-alkyl, substituted S-alkyl, S-aryl, and S-heteroaryl, each being optionally substituted with a substituent chosen from (C1-C3)alkyl, halogen, and O—(C1-C3)alkyl.

13. A compound according to claim 10, wherein A is substituted with a second substituent selected from the group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, and N(R8)(R9); in which R8 and R9 are independently chosen from H, (C1-C3)alkyl, halogenated (C1-C3)alkyl, (C1-C3)alkylOH, (C1-C3)alkylNH$_2$, (C1-C3)alkylCOOM, and (C1-C3)alkylSO$_3$M; in which, when R8 and R9 are simultaneously different from H, they may be linked to form a 5- to 7-membered ring containing from 0 to 3 heteroatoms chosen from N, O and S; in which M is H or an alkali metal cation chosen from Li, Na and K; and in which R10 is H or an optionally substituted nonaromatic heterocycle comprising 2 to 7 carbon atoms, and 1 to 3 heteroatoms chosen from N, O and S.

14. A compound according to claim 12, wherein A is substituted with a second substituent selected from the group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, and N(R8)(R9); in which R8 and R9 are independently chosen from H, (C1-C3)alkyl, halogenated (C1-C3)alkyl, (C1-C3)alkylOH, (C1-C3)alkylNH$_2$, (C1-C3)alkylCOOM, and (C1-C3)alkylSO$_3$M; in which, when R8 and R9 are simultaneously different from H, they may be linked to form a 5- to 7-membered ring containing from 0 to 3 heteroatoms chosen from N, O and S; in which M is H or an alkali metal cation chosen from Li, Na and K; and in which R10 is H or an optionally substituted nonaromatic heterocycle comprising 2 to 7 carbon atoms, and 1 to 3 heteroatoms chosen from N, O and S.

15. A compound according to claim 10, wherein A is phenyl, pyrazolyl or isoxazolyl substituted with one or two substituents selected from halogen, (C1-C4)alkyl, halogenated (C1-C3)alkyl, O—(C1-C4)alkyl, S—(C1-C4)alkyl, halogenated O—(C1-C4)alkyl and halogenated S—(C1-C4)alkyl, and when A is disubstituted, the two substituents may be linked to each other to form a 5- to 7-membered ring containing from 0 to 3 heteroatoms chosen from O, N and S.

16. A compound according to claim 1, selected from the group consisting of:
- 4-{4-[3-(2-fluoro-5-trifluoromethylphenyl)ureido]phenyl}-1H-pyrrole-3-carboxamide,
- 1-acetyl-2-amino-4-{4-[3-(2-fluoro-5-trifluoromethylphenyl)ureido]phenyl}-1H-pyrrole-3-carboxamide,
- 2-formylamino-4-{4-[3-(2-fluoro-5-trifluoromethylphenyl)ureido]phenyl}-1H-pyrrole-3-carboxamide,
- 2-isobutyrylamino-4-{4-[3-(2-fluoro-5-trifluoromethylphenyl)ureido]phenyl}-1H-pyrrole-3-carboxamide,
- 2-butyrylamino-4-{4-[3-(2-fluoro-5-trifluoromethylphenyl)ureido]phenyl}-1H-pyrrole-3-carboxamide,
- 2-(3-cyclopentylpropionylamino)-4-{4-[3-(2-fluoro-5-trifluoromethylphenyl)-ureido]phenyl}--1H-pyrrole-3-carboxamide,
- 2-(cyclopropylcarbonylamino)-4-{4-[3-(2-fluoro-5-trifluoromethylphenyl)-ureido]phenyl}--1H-pyrrole-3-carboxamide,
- 2-pivaloylamino-4-{4-[3-(2-fluoro-5-trifluoromethylphenyl)ureido]phenyl}-1H-pyrrole-3-carboxamide,
- 2-(2-dimethylaminoacetylamino)-4-{4-[3-(2-fluoro-5-trifluoromethylphenyl)-ureido]phenyl}-1H-pyrrole-3-carboxamide,
- 2-acetylamino-4-{6-[3-(2-fluoro-5-trifluoromethylphenyl)ureido]pyridin-3-yl}-1H-pyrrole-3-carboxamide,
- 2-(3-ethylureido)-4-{4-[3-(2-fluoro-5-trifluoromethylphenyl)ureido]phenyl}-1H-pyrrole-3-carboxamide,
- 2-acetylamino-4-{4-[3-(3-fluoro-5-trifluoromethylphenyl)ureido]phenyl}-1H-pyrrole-3-carboxamide,
- 2-acetylamino-4-{4-[3-(3-ethylphenyl)ureido]phenyl}-1H-pyrrole-3-carboxamide,
- 2-acetylamino-4-{4-[3-(4-fluoro-3-trifluoromethylphenyl)ureido]phenyl}-1H-pyrrole-3-carboxamide,
- 2-acetylamino-4-{4-[3-(3-fluorophenyl)ureido]phenyl}-1H-pyrrole-3-carboxamide,
- 2-acetylamino-4-{4-[3-(4-fluorophenyl)ureido]phenyl}-1H-pyrrole-3-carboxamide,
- 2-acetylamino-4-{4-[3-(2-fluorophenyl)ureido]phenyl}-1H-pyrrole-3-carboxamide,
- 2-acetylamino-4-{4-[3-(4-difluoromethoxyphenyl)ureido]phenyl}-1H-pyrrole-3-carboxamide,
- 2-acetylamino-4-{4-[3-(3,4-dimethylphenyl)ureido]phenyl}-1H-pyrrole-3-carboxamide,
- 2-acetylamino-4-{4-[3-(3,4-dimethoxyphenyl)ureido]phenyl}-1H-pyrrole-3-carboxamide,
- 2-acetylamino-4-{4-[3-(4trifluoromethoxyphenyl)ureido]phenyl}-1H-pyrrole-3-carboxamide,
- 2-acetylamino-4-{4-[3-(2,5-dimethoxyphenyl)ureido]phenyl}-1H-pyrrole-3-carboxamide,
- 2-acetylamino-4-[4-(3-phenylureido)phenyl]-1H-pyrrole-3-carboxamide,
- 2-acetylamino-4-{4-[3-(2-methoxyphenyl)ureido]phenyl}-1H-pyrrole-3-carboxamide,
- 2-acetylamino-4-{4-[3-(2-trifluoromethylphenyl)ureido]phenyl}-1H-pyrrole-3-carboxamide,
- 2-acetylamino-4-[4-(3-o-tolylureido)phenyl]-1H-pyrrole-3-carboxamide,
- 2-acetylamino-4-{4-[3-(3-methoxyphenyl)ureido]phenyl}-1H-pyrrole-3-carboxamide,
- 2-acetylamino-4-{4-[3-(3-trifluoromethylphenyl)ureido]phenyl}-1H-pyrrole-3-carboxamide,
- 2-acetylamino-4-[4-(3-m-tolylureido)phenyl]-1H-pyrrole-3-carboxamide
- 2-acetylamino-4-{4-[3-(4-trifluoromethylphenyl)ureido]phenyl}-1H-pyrrole-3-carboxamide,
- 2-acetylamino-4-[4-(3-p-tolylureido)phenyl]-1H-pyrrole-3-carboxamide,
- 2-acetylamino-4-{4-[3-(4-chloro-3-trifluoromethylphenyl)ureido]phenyl}-1H-pyrrole-3-carboxamide,
- 2-acetylamino-4-{4-[3-(2-chloro-5-trifluoromethylphenyl)ureido]phenyl}-1H-pyrrole-3-carboxamide,
- 2-acetylamino-4-{4-[3-(2-fluoro-3-trifluoromethylphenyl)ureido]phenyl}-1H-pyrrole-3-carboxamide,
- 2-acetylamino-4-{4-[3-(3-chloro-4-difluoromethoxyphenyl)ureido]phenyl}-1H-pyrrole-3-carboxamide,
- 2-acetylamino-4-{4-[3-(3,5-dimethoxyphenyl)ureido]phenyl}-1H-pyrrole-3-carboxamide,
- 2-acetylamino-4-{4-[3-(3,5-dimethylphenyl)ureido]phenyl}-1H-pyrrole-3-carboxamide,
- 2-acetylamino-4-{4-[3-(2,5-dimethylphenyl)ureido]phenyl}-1H-pyrrole-3-carboxamide,
- 2-acetylamino-4-{4-[3-(2-methoxy-5-methylphenyl)ureido]phenyl}-1H-pyrrole-3-carboxamide,
- 2-acetylamino-4-{4-[3-(4-methyl-3-trifluoromethylphenyl)ureido]phenyl}-1H-pyrrole-3-carboxamide, and
- 2-acetylamino-4-[4-(2,3-dichlorobenzenesulphonylamino)phenyl]-1H-pyrrole-3-carboxamide; or a pharmaceutically acceptable salt thereof.

17. A pharmaceutical composition comprising a compound according to claim 1, in combination with a pharmaceutically acceptable excipient.

18. A pharmaceutical composition comprising a compound according to claim 15, in combination with a pharmaceutically acceptable excipient.

19. A pharmaceutical composition comprising a compound according to claim 16, in combination with a pharmaceutically acceptable excipient.

20. A method for inhibiting a reaction catalysed by a kinase selected from the group consisting of FAK, KDR and Tie2, said method comprising contacting said kinase with an effective amount of a compound according to claim 1.

* * * * *

UNITED STATES PATENT AND TRADEMARK OFFICE
CERTIFICATE OF CORRECTION

PATENT NO. : 7,592,365 B2  Page 1 of 1
APPLICATION NO. : 11/832208
DATED : September 22, 2009
INVENTOR(S) : Baptiste Ronan et al.

It is certified that error appears in the above-identified patent and that said Letters Patent is hereby corrected as shown below:

In column 4, line 33, delete "idarjbicin, epirjbicin," and insert -- idarubicin, epirubicin, --, therefor.

In column 17, line 11, delete "dichiloromethane]." and insert -- dichloromethane]. --, therefor.

In column 18, line 42, delete "s 2H);" and insert -- s: 2H); --, therefor.

In column 19, line 50, delete "m/z 182" and insert -- m/z=182 --, therefor.

In column 20, line 19, delete "trifiloromethylphenyl" and insert -- trifluoromethylphenyl --, therefor.

In column 28, line 5-7, delete "2-Amino-1-(6-nitropyridin-3-yl)ethanone may be prepared in the following manner:" and insert the same on Col. 28, line 6 as a new paragraph.

In column 51, line 25-26, in Claim 1, delete "CH$_2$—NH—CO —NH," and insert -- CH$_2$—NH—CO—NH, --, therefor.

In column 51, line 31, in Claim 1, delete "R1)" and insert -- R1 --, therefor.

In column 51, line 36, in Claim 1, delete "R"5and" and insert -- R"5 and --, therefor.

In column 51, line 65, in Claim 2, delete "R1is" and insert -- R1 is --, therefor.

In column 53, line 27, in Claim 16, delete "phenyl}--1H" and insert -- phenyl}-1H --, therefor.

In column 53, line 30, in Claim 16, delete "phenyl}--1H" and insert -- phenyl}-1H --, therefor.

In column 54, line 1, in Claim 16, delete "(4trifluoromethoxyphenyl)" and insert -- (4-trifluoromethoxyphenyl) --, therefor.

Signed and Sealed this

Seventeenth Day of August, 2010

David J. Kappos
*Director of the United States Patent and Trademark Office*